(12) United States Patent
Legrand et al.

(10) Patent No.: US 7,560,527 B1
(45) Date of Patent: *Jul. 14, 2009

(54) MODIFIED ADENOVIRUS FIBRE AND USES

(75) Inventors: Valérie Legrand, Strasbourg (FR); Philippe Leissner, Caluire et Cuire (FR)

(73) Assignee: Transgene S.A., Strasbourg (FR)

( * ) Notice: Subject to any disclaimer, the term of this patent is extended or adjusted under 35 U.S.C. 154(b) by 800 days.

This patent is subject to a terminal disclaimer.

(21) Appl. No.: 10/130,786

(22) PCT Filed: Nov. 23, 2000

(86) PCT No.: PCT/FR00/03263

§ 371 (c)(1),
(2), (4) Date: Oct. 2, 2002

(87) PCT Pub. No.: WO01/38361

PCT Pub. Date: May 31, 2001

(51) Int. Cl.
*C07K 1/00* (2006.01)
*A61K 48/00* (2006.01)
*C12N 7/00* (2006.01)
*C12N 7/01* (2006.01)
*C12N 15/00* (2006.01)
*C12N 15/10* (2006.01)

(52) U.S. Cl. .................. 530/350; 424/93.2; 435/173.3; 435/69.1; 435/320.1; 435/456; 536/23.1

(58) Field of Classification Search .................. None
See application file for complete search history.

(56) References Cited

U.S. PATENT DOCUMENTS 5,928,944 A * 7/1999 Seth et al. .................. 435/375

FOREIGN PATENT DOCUMENTS

| FR | 2 761 689 | 10/1998 |
|----|-----------|---------|
| WO | WO 98/07865 | 2/1998 |
| WO | WO 99/39734 | 8/1999 |
| WO | WO 00/15823 | 3/2000 |

OTHER PUBLICATIONS

Protein structure prediction- Wikipedia, downloaded Oct. 14, 2005.*
Tertiary structures- Biology Pages, downloaded Oct. 14, 2005.*
Smith et al, Surface point mutations that significantly alter the structure and stability of a protein's denatured state, Protein Science, 1996, vol. 5, pp. 2009-2019.*
Hong and Engler, Domains Required for Assembly of Adenovirus Type 2 Fiber Trimers, J Virology, 1996, vol. 70(10), pp. 7071-7078.*
Xia et al, Crystal Structure of the receptor binding domain of adenovirus type 5 fiberprotein at 1.7A resolution, Strcutre, 1994,vol. 2(12), abstract, downloaded Mar. 3, 2006.*
Durmort et al, Structure of the Fiber Head of Ad3, a Non-CAR-Binding Serotype of Adenovirus, Virology, 2001, vol. 285, pp. 302-312.*
Bewley et al, Structural Analysis of the Mechanism of Adenovirus Binding to its Human Cellular Receptor, CAR, Science, 1999, vol. 286, pp. 1579-1583.*
Chiu et al, Structural Analysis of a Fiber Pseudotyped Adenovirus with Ocular Tropsim Suggests Differential Modes of Cell Receptor Interaction, 2001, vol. 75911),pp. 5375-5380.*
Burmeister et al, Crystal Structure of Species D Adenovirus Fiber Knobs and Their Sialic Acid Binding Sites, 2004, vol. 78(14), pp. 7727-7736.*
Kirby et al, Adenovirus Type 9 Fiber Knob Binds to the Coxsackie B Virus-Adenovirus Receptor (CAR) with Lower Affinity than Fiber Knobs of Other CAR-Binding Adenovirus Serotypes, J Virology, 2001, vol. 75(15), pp. 7210-7214.*
Facing page, J Virology, Nov. 1999, vol. 73(11), showing stamp that received Oct. 16, 1999.*
Santis et al, Molecular determinants of adenovirus serotype 5 fibre binding to its cellular receptor CAR, J General Virology, 1999 vol. 80, pp. 1519-1527.*
CAR-dependent and CAR-independent pathways of adenovirus vector-mediated gene transfer and expression in human fibroblasts, The Journal of Clinical Investigation, 1999, vol. 103 (4), 579-587.*
Fornasari et al, Quaternary Structure Constraints on Evolutionary Sequence Divergence, Mol. Biol. Evol. 24(2):349-351. 2007.*
I. Kirby et al., *Journal of Virology*, vol. 73, No. 11, pp. 9508-9514, Oct. 8, 1999.
J. Chroboczek et al, *Current Topics in Microbiology and Immunology*, vol. 199, 1995, pp. 163-200.
V.N. Krasnykh et al., *J. of Virology, U.S., The American Society for Microbiology*, vol. 70, No. 10, Oct. 1, 1996, pp. 6839-6846.

* cited by examiner

*Primary Examiner*—Maria B Marvich
(74) *Attorney, Agent, or Firm*—Buchanan, Ingersoll & Rooney, PC

(57) ABSTRACT

The invention concerns an adenovirus fiber modified by mutation of one or several residues of the region included between residues 491 and 505 of SEQ ID NO: 1, the viral particles or pseudo-particles comprising such a fiber and their uses.

17 Claims, No Drawings

SEQUENCE LISTING

```
<160> NUMBER OF SEQ ID NOS: 57

<210> SEQ ID NO 1
<211> LENGTH: 581
<212> TYPE: PRT
<213> ORGANISM: Mastadenovirus

<400> SEQUENCE: 1

Met Lys Arg Ala Arg Pro Ser Glu Asp Thr Phe Asn Pro Val Tyr Pro
  1               5                  10                  15

Tyr Asp Thr Glu Thr Gly Pro Pro Thr Val Pro Phe Leu Thr Pro Pro
                 20                  25                  30

Phe Val Ser Pro Asn Gly Phe Gln Glu Ser Pro Pro Gly Val Leu Ser
             35                  40                  45

Leu Arg Leu Ser Glu Pro Leu Val Thr Ser Asn Gly Met Leu Ala Leu
         50                  55                  60

Lys Met Gly Asn Gly Leu Ser Leu Asp Glu Ala Gly Asn Leu Thr Ser
 65                  70                  75                  80

Gln Asn Val Thr Thr Val Ser Pro Pro Leu Lys Lys Thr Lys Ser Asn
                 85                  90                  95

Ile Asn Leu Glu Ile Ser Ala Pro Leu Thr Val Thr Ser Glu Ala Leu
                100                 105                 110
```

```
Thr Val Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
130                 135                 140

Ala Thr Gln Gly Pro Leu Thr Val Ser Glu Gly Lys Leu Ala Leu Gln
145                 150                 155                 160

Thr Ser Gly Pro Leu Thr Thr Thr Asp Ser Thr Leu Thr Ile Thr
                165                 170                 175

Ala Ser Pro Pro Leu Thr Thr Ala Thr Gly Ser Leu Gly Ile Asp Leu
                180                 185                 190

Lys Glu Pro Ile Tyr Thr Gln Asn Gly Lys Leu Gly Leu Lys Tyr Gly
                195                 200                 205

Ala Pro Leu His Val Thr Asp Asp Leu Asn Thr Leu Thr Val Ala Thr
                210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val
                260                 265                 270

Ser Tyr Pro Phe Asp Ala Gln Asn Gln Leu Asn Leu Arg Leu Gly Gln
                275                 280                 285

Gly Pro Leu Phe Ile Asn Ser Ala His Asn Leu Asp Ile Asn Tyr Asn
                290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asp Ala Thr Ala Ile
                325                 330                 335

Ala Ile Asn Ala Gly Asp Gly Leu Glu Phe Gly Ser Pro Asn Ala Pro
                340                 345                 350

Asn Thr Asn Pro Leu Lys Thr Lys Ile Gly His Gly Leu Glu Phe Asp
                355                 360                 365

Ser Asn Lys Ala Met Val Pro Lys Leu Gly Thr Gly Leu Ser Phe Asp
370                 375                 380

Ser Thr Gly Ala Ile Thr Val Gly Asn Lys Asn Asp Lys Leu Thr
385                 390                 395                 400

Leu Trp Thr Thr Pro Ala Pro Ser Pro Asn Cys Arg Leu Asn Ala Glu
                405                 410                 415

Lys Asp Ala Lys Leu Thr Leu Val Leu Thr Lys Cys Gly Ser Gln Ile
                420                 425                 430

Leu Ala Thr Val Ser Val Leu Ala Val Lys Gly Ser Leu Ala Pro Ile
                435                 440                 445

Ser Gly Thr Val Gln Ser Ala His Leu Ile Ile Arg Phe Asp Glu Asn
                450                 455                 460

Gly Val Leu Leu Asn Asn Ser Phe Leu Asp Pro Glu Tyr Trp Asn Phe
465                 470                 475                 480

Arg Asn Gly Asp Leu Thr Glu Gly Thr Ala Tyr Thr Asn Ala Val Gly
                485                 490                 495

Phe Met Pro Asn Leu Ser Ala Tyr Pro Lys Ser His Gly Lys Thr Ala
                500                 505                 510

Lys Ser Asn Ile Val Ser Gln Val Tyr Leu Asn Gly Asp Lys Thr Lys
                515                 520                 525
```

-continued

```
Pro Val Thr Leu Thr Ile Thr Leu Asn Gly Thr Gln Glu Thr Gly Asp
    530                 535                 540

Thr Thr Pro Ser Ala Tyr Ser Met Ser Phe Ser Trp Asp Trp Ser Gly
545                 550                 555                 560

His Asn Tyr Ile Asn Glu Ile Phe Ala Thr Ser Ser Tyr Thr Phe Ser
                565                 570                 575

Tyr Ile Ala Gln Glu
            580

<210> SEQ ID NO 2
<211> LENGTH: 60
<212> TYPE: DNA
<213> ORGANISM: Artificial sequence
<220> FEATURE:
<223> OTHER INFORMATION: Description of artificial sequence : Primer -
      Synthetic oligonucleotide oTG7000 (coding for PSASASASAPGS).

<400> SEQUENCE: 2
aacgattctt tagctgccgg gagcagaggc ggaggcggag gcgctgggtt cttgggcaat    60

<210> SEQ ID NO 3
<211> LENGTH: 57
<212> TYPE: DNA
<213> ORGANISM: Artificial sequence
<220> FEATURE:
<223> OTHER INFORMATION: Description of artificial sequence : Primer -
      Synthetic oligonucleotide oTG7001 (coding for GRP).

<400> SEQUENCE: 3
aacgattctt tacatcaggt ggcccacagc ccagtggttt ccgctgccgg gagcaga       57

<210> SEQ ID NO 4
<211> LENGTH: 20
<212> TYPE: DNA
<213> ORGANISM: Artificial sequence
<220> FEATURE:
<223> OTHER INFORMATION: Description of artificial sequence : Primer -
      Synthetic oligonucleotide oTG10776.

<400> SEQUENCE: 4
ccttccacgg gaagattgta                                                20

<210> SEQ ID NO 5
<211> LENGTH: 20
<212> TYPE: DNA
<213> ORGANISM: Artificial sequence
<220> FEATURE:
<223> OTHER INFORMATION: Description of artificial sequence : Primer -
      Synthetic oligonucleotide oTG10781.

<400> SEQUENCE: 5
ggggtgtctg tcttcacact                                                20

<210> SEQ ID NO 6
<211> LENGTH: 26
<212> TYPE: DNA
<213> ORGANISM: Artificial sequence
<220> FEATURE:
<223> OTHER INFORMATION: Description of artificial sequence : Primer -
      Synthetic oligonucleotide oTG11065.

<400> SEQUENCE: 6
gggaagcttg aggttaacct aagcac                                         26

<210> SEQ ID NO 7
```

```
<211> LENGTH: 28
<212> TYPE: DNA
<213> ORGANISM: Artificial sequence
<220> FEATURE:
<223> OTHER INFORMATION: Description of artificial sequence : Primer -
      Synthetic oligonucleotide oTG11066.

<400> SEQUENCE: 7
gggtctagag ctgccgggag cagaggcg                                          28

<210> SEQ ID NO 8
<211> LENGTH: 29
<212> TYPE: DNA
<213> ORGANISM: Artificial sequence
<220> FEATURE:
<223> OTHER INFORMATION: Description of artificial sequence : Primer -
      Synthetic oligonucleotide oTG11067.

<400> SEQUENCE: 8
gggctcgagt tatgtttcaa cgtgtttat                                         29

<210> SEQ ID NO 9
<211> LENGTH: 24
<212> TYPE: DNA
<213> ORGANISM: Artificial sequence
<220> FEATURE:
<223> OTHER INFORMATION: Description of artificial sequence : Primer -
      Synthetic oligonucleotide oTG11068.

<400> SEQUENCE: 9
gtgcccgggg agtttattaa tatc                                              24

<210> SEQ ID NO 10
<211> LENGTH: 31
<212> TYPE: DNA
<213> ORGANISM: Artificial sequence
<220> FEATURE:
<223> OTHER INFORMATION: Description of artificial sequence : Primer -
      Synthetic oligonucleotide oTG11069 (cloning EGF) from Homo
      sapiens.

<400> SEQUENCE: 10
gcgtctagaa atagtgactc tgaatgtccc c                                      31

<210> SEQ ID NO 11
<211> LENGTH: 46
<212> TYPE: DNA
<213> ORGANISM: Artificial sequence
<220> FEATURE:
<223> OTHER INFORMATION: Description of artificial sequence : Primer -
      Synthetic oligonucleotide oTG11070 (EGF cloning) from Homo
      sapiens.

<400> SEQUENCE: 11
gcgctcgagc acaaacgatt ctttagcgca gttcccacca cttcag                      46

<210> SEQ ID NO 12
<211> LENGTH: 42
<212> TYPE: DNA
<213> ORGANISM: Artificial sequence
<220> FEATURE:
<223> OTHER INFORMATION: Description of artificial sequence : Primer -
      Synthetic oligonucleotide oTG7414 (deletion of the sheet D) from
      Mastadenovirus.

<400> SEQUENCE: 12
tagcactcca ttttcgtcgg atccttgaac tgttccagat at                          42
```

```
<210> SEQ ID NO 13
<211> LENGTH: 43
<212> TYPE: DNA
<213> ORGANISM: Artificial sequence
<220> FEATURE:
<223> OTHER INFORMATION: Description of artificial sequence : Primer -
      Synthetic oligonucleotide oTGA (deletion of the loop CD) from
      Mastadenovirus.

<400> SEQUENCE: 13
cttataataa gatgagcact ggatccagcc aaaactgaaa ctg                    43

<210> SEQ ID NO 14
<211> LENGTH: 45
<212> TYPE: DNA
<213> ORGANISM: Artificial sequence
<220> FEATURE:
<223> OTHER INFORMATION: Description of artificial sequence : Primer -
      Synthetic oligonucleotide oTGB (deletion  of the loop CD and f.D)
      from Mastadenovirus.

<400> SEQUENCE: 14
gtagcactcc attttcgtcg gatccaacag ccaaaactga aactg                  45

<210> SEQ ID NO 15
<211> LENGTH: 88
<212> TYPE: DNA
<213> ORGANISM: Artificial sequence
<220> FEATURE:
<223> OTHER INFORMATION: Description of artificial sequence : Primer -
      Synthetic oligonucleotide oTG11135 (loop CD5 to CD3) from
      Mastadenovirus.

<400> SEQUENCE: 15
cgtcaaatct tataataaga tgagcactca cgttttttgtt tttaaacagg gtgttgtagt    60
cgctaacagc caaaactgaa actgtagc                                       88

<210> SEQ ID NO 16
<211> LENGTH: 64
<212> TYPE: DNA
<213> ORGANISM: Artificial sequence
<220> FEATURE:
<223> OTHER INFORMATION: Description of artificial sequence : Primer -
      Synthetic oligonucleotide oTG10350 (sheet D5 to D3) from
      Mastadenovirus.

<400> SEQUENCE: 16
gtagcactcc attttcgtca aagtagagct ccacgttgat actttgaact gttccagata    60
ttgg                                                                 64

<210> SEQ ID NO 17
<211> LENGTH: 88
<212> TYPE: DNA
<213> ORGANISM: Artificial sequence
<220> FEATURE:
<223> OTHER INFORMATION: Description of artificial sequence : Primer -
      Synthetic oligonucleotide oTG11136 (CD+D5 to CD+D3) from
      Mastadenovirus.

<400> SEQUENCE: 17
cgtcaaagta gagctccacg ttgatactca cgttttttgtt tttaaacagg gtgttgtagt    60
cgctaacagc caaaactgaa actgtagc                                       88

<210> SEQ ID NO 18
<211> LENGTH: 56
```

<210> SEQ ID NO 18
<211> LENGTH: 56
<212> TYPE: DNA
<213> ORGANISM: Artificial sequence
<220> FEATURE:
<223> OTHER INFORMATION: Description of artificial sequence : Primer - Synthetic oligonucleotide oTGC (replacement bend GSLA to DKLT) from Mastadenovirus.

<400> SEQUENCE: 18
ttgaactgtt ccagatattg gggtcagttt gtctttaaca gccaaaactg aaactg        56

<210> SEQ ID NO 19
<211> LENGTH: 48
<212> TYPE: DNA
<213> ORGANISM: Artificial sequence
<220> FEATURE:
<223> OTHER INFORMATION: Description of artificial sequence : Primer - Synthetic oligonucleotide oTGD (replacement bend SGTV to DLKT) from Mastadenovirus.

<400> SEQUENCE: 19
aataagatga gcactttggg tcagtttgtc tattggagcc aaactgcc                 48

<210> SEQ ID NO 20
<211> LENGTH: 44
<212> TYPE: DNA
<213> ORGANISM: Artificial sequence
<220> FEATURE:
<223> OTHER INFORMATION: Description of artificial sequence : Primer - Synthetic oligonucleotide oTGE (replacement G443 to D) from Mastadenovirus.

<400> SEQUENCE: 20
ccagatattg gagccaaact gtctttaaca gccaaaactg aaac                     44

<210> SEQ ID NO 21
<211> LENGTH: 42
<212> TYPE: DNA
<213> ORGANISM: Artificial sequence
<220> FEATURE:
<223> OTHER INFORMATION: Description of artificial sequence : Primer - Synthetic oligonucleotide oTGF (replacement L445 to F) from Mastadenovirus.

<400> SEQUENCE: 21
tgttccagat attggagcga aactgccttt aacagccaaa ac                       42

<210> SEQ ID NO 22
<211> LENGTH: 42
<212> TYPE: DNA
<213> ORGANISM: Artificial sequence
<220> FEATURE:
<223> OTHER INFORMATION: Description of artificial sequence : Primer - Synthetic oligonucleotide oTGG (replacement G450 to N) from Mastadenovirus.

<400> SEQUENCE: 22
atgagcactt tgaactgtgt tagatattgg agccaaactg cc                       42

<210> SEQ ID NO 23
<211> LENGTH: 44
<212> TYPE: DNA
<213> ORGANISM: Artificial sequence
<220> FEATURE:
<223> OTHER INFORMATION: Description of artificial sequence : Primer - Synthetic oligonucleotide oTGH (replacement T451 to K) from Mastadenovirus.

<400> SEQUENCE: 23

-continued

```
taagatgagc actttgaacc tttccagata ttggagccaa actg                44
```

<210> SEQ ID NO 24
<211> LENGTH: 45
<212> TYPE: DNA
<213> ORGANISM: Artificial sequence
<220> FEATURE:
<223> OTHER INFORMATION: Description of artificial sequence : Primer -
      Synthetic oligonucleotide oTGI (replacement V452 to N) from
      Mastadenovirus

<400> SEQUENCE: 24

```
cttataataa gatgagcact ttggtttgtt ccagatattg gagcc               45
```

<210> SEQ ID NO 25
<211> LENGTH: 48
<212> TYPE: DNA
<213> ORGANISM: Artificial sequence
<220> FEATURE:
<223> OTHER INFORMATION: Description of artificial sequence : Primer -
      Synthetic oligonucleotide oTGJ (replacement A455 to F) from
      Mastadenovirus.

<400> SEQUENCE: 25

```
gtcaaatctt ataataagat ggaaactttg aactgttcca gatattgg            48
```

<210> SEQ ID NO 26
<211> LENGTH: 47
<212> TYPE: DNA
<213> ORGANISM: Artificial sequence
<220> FEATURE:
<223> OTHER INFORMATION: Description of artificial sequence : Primer -
      Synthetic oligonucleotide oTGK (replacement L457 to A) from
      Mastadenovirus.

<400> SEQUENCE: 26

```
ccattttcgt caaatcttat aattttatga gcactttgaa ctgttcc             47
```

<210> SEQ ID NO 27
<211> LENGTH: 46
<212> TYPE: DNA
<213> ORGANISM: Artificial sequence
<220> FEATURE:
<223> OTHER INFORMATION: Description of artificial sequence : Primer -
      Synthetic oligonucleotide oTGL (replacement I459 to A) from
      Mastadenovirus.

<400> SEQUENCE: 27

```
gcactccatt ttcgtcaaat ctagcaataa gatgagcact ttgaac              46
```

<210> SEQ ID NO 28
<211> LENGTH: 23
<212> TYPE: DNA
<213> ORGANISM: Artificial sequence
<220> FEATURE:
<223> OTHER INFORMATION: Description of artificial sequence : Primer -
      Synthetic oligonucleotide oTG11102 (hexon cloning) from
      Mastadenovirus.

<400> SEQUENCE: 28

```
cggttcatcc ctgtggaccg tga                                       23
```

<210> SEQ ID NO 29
<211> LENGTH: 38
<212> TYPE: DNA
<213> ORGANISM: Artificial sequence
<220> FEATURE:
<223> OTHER INFORMATION: Description of artificial sequence : Primer -

Synthetic oligonucleotide oTG11103 (hexon cloning) from
Mastadenovirus.

<400> SEQUENCE: 29
ggcctctaga gttgagaaaa attgcatttc cacttgac                    38

<210> SEQ ID NO 30
<211> LENGTH: 23
<212> TYPE: DNA
<213> ORGANISM: Artificial sequence
<220> FEATURE:
<223> OTHER INFORMATION: Description of artificial sequence : Primer -
    Synthetic oligonucleotide oTG11104 (hexon cloning) from
    Mastadenovirus.

<400> SEQUENCE: 30
ggtattgtac agtgaagatg tag                                    23

<210> SEQ ID NO 31
<211> LENGTH: 23
<212> TYPE: DNA
<213> ORGANISM: Artificial sequence
<220> FEATURE:
<223> OTHER INFORMATION: Description of artificial sequence : Primer -
    Synthetic oligonucleotide oTG11105 from Mastadenovirus.

<400> SEQUENCE: 31
cgttggaagg actgtacttt agc                                    23

<210> SEQ ID NO 32
<211> LENGTH: 38
<212> TYPE: DNA
<213> ORGANISM: Artificial sequence
<220> FEATURE:
<223> OTHER INFORMATION: Description of artificial sequence : Primer -
    Synthetic oligonucleotide oTG11106 (cDNA EGF cloning) from Homo
    sapiens.

<400> SEQUENCE: 32
cgcgtctaga ggcgaatagt gactctgaat gtccoctg                    38

<210> SEQ ID NO 33
<211> LENGTH: 45
<212> TYPE: DNA
<213> ORGANISM: Artificial sequence
<220> FEATURE:
<223> OTHER INFORMATION: Description of artificial sequence : Primer -
    Synthetic oligonucleotide oTG11107 (cDNA EGF cloning) from Homo
    sapiens.

<400> SEQUENCE: 33
ccactgtaca ataccacttt agggcgcagt tcccaccact tcagg             45

<210> SEQ ID NO 34
<211> LENGTH: 21
<212> TYPE: DNA
<213> ORGANISM: Artificial sequence
<220> FEATURE:
<223> OTHER INFORMATION: Description of artificial sequence : Primer -
    Synthetic oligonucleotide oTG7171 (deletion of the fiber) from
    Mastadenovirus.

<400> SEQUENCE: 34
atggttaact tgcaccagtg c                                      21

<210> SEQ ID NO 35
<211> LENGTH: 27

```
<212> TYPE: DNA
<213> ORGANISM: Artificial sequence
<220> FEATURE:
<223> OTHER INFORMATION: Description of artificial sequence : Primer -
      Synthetic oligonucleotide oTG7275 (deletion of the fiber) from
      Mastadenovirus.

<400> SEQUENCE: 35
gggctcgagc tgcaacaaca tgaagat                                              27

<210> SEQ ID NO 36
<211> LENGTH: 27
<212> TYPE: DNA
<213> ORGANISM: Artificial sequence
<220> FEATURE:
<223> OTHER INFORMATION: Description of artificial sequence : Primer -
      Synthetic oligonucleotide oTG7276 (deletion of the fiber) from
      Mastadenovirus.

<400> SEQUENCE: 36
ccgctcgaga ctcctccctt tgtatcc                                              27

<210> SEQ ID NO 37
<211> LENGTH: 20
<212> TYPE: DNA
<213> ORGANISM: Artificial sequence
<220> FEATURE:
<223> OTHER INFORMATION: Description of artificial sequence : Primer -
      Synthetic oligonucleotide oTG7049 (deletion of the fiber) from
      Mastadenovirus.

<400> SEQUENCE: 37
ctgcccggga gtttattaat                                                      20

<210> SEQ ID NO 38
<211> LENGTH: 72
<212> TYPE: DNA
<213> ORGANISM: Artificial sequence
<220> FEATURE:
<223> OTHER INFORMATION: Description of artificial sequence : Primer -
      Synthetic oligonucleotide oTG11992.

<400> SEQUENCE: 38
cataacacaa acgattcttt atgttcgtgt tggtggttct cgagcgcaat agctgccggg          60
agcagaggcg ga                                                              72

<210> SEQ ID NO 39
<211> LENGTH: 57
<212> TYPE: DNA
<213> ORGANISM: Artificial sequence
<220> FEATURE:
<223> OTHER INFORMATION: Description of artificial sequence : Primer -
      Synthetic oligonucleotide oTG11991.

<400> SEQUENCE: 39
cataacacaa acgattcttt aatatacgtc tagatagctg ccgggagcag aggcgga            57

<210> SEQ ID NO 40
<211> LENGTH: 42
<212> TYPE: DNA
<213> ORGANISM: Artificial sequence
<220> FEATURE:
<223> OTHER INFORMATION: Description of artificial sequence : Primer -
      Synthetic oligonucleotide oTG12499 from Mastadenovirus.

<400> SEQUENCE: 40
gcatttagtc tacagttagg ctctggagct ggtgtggtcc ac                             42
```

<210> SEQ ID NO 41
<211> LENGTH: 39
<212> TYPE: DNA
<213> ORGANISM: Artificial sequence
<220> FEATURE:
<223> OTHER INFORMATION: Description of artificial sequence : Primer - Synthetic oligonucleotide oTG12498 from Mastadenovirus.

<400> SEQUENCE: 41
gtctacagtt aggagatggc tttggtgtgg tccacaaag                        39

<210> SEQ ID NO 42
<211> LENGTH: 47
<212> TYPE: DNA
<213> ORGANISM: Artificial sequence
<220> FEATURE:
<223> OTHER INFORMATION: Description of artificial sequence : Primer - Synthetic oligonucleotide oTG12740 from Mastadenovirus.

<400> SEQUENCE: 42
ctacagttag gagatggagc gggcccggtc cacaaagtta gcttatc               47

<210> SEQ ID NO 43
<211> LENGTH: 59
<212> TYPE: DNA
<213> ORGANISM: Artificial sequence
<220> FEATURE:
<223> OTHER INFORMATION: Description of artificial sequence : Primer - Synthetic oligonucleotide oTG12125 from Mastadenovirus.

<400> SEQUENCE: 43
cacaaacgat tctttacttc ttcttttct tcttttgga tccgggagca gaggcggag    59

<210> SEQ ID NO 44
<211> LENGTH: 72
<212> TYPE: DNA
<213> ORGANISM: Artificial sequence
<220> FEATURE:
<223> OTHER INFORMATION: Description of artificial sequence : Primer - Synthetic oligonucleotide oTG11992 from Mastadenovirus.

<400> SEQUENCE: 44
cataacacaa acgattcttt atgttcgtgt tggtggttct cgagcgcaat agctgccggg  60
agcagaggcg ga                                                     72

<210> SEQ ID NO 45
<211> LENGTH: 57
<212> TYPE: DNA
<213> ORGANISM: Artificial sequence
<220> FEATURE:
<223> OTHER INFORMATION: Description of artificial sequence : Primer - Synthetic oligonucleotide oTG1199 from Mastadenovirus.

<400> SEQUENCE: 45
cataacacaa acgattcttt aatatacgtc tagatagctg ccgggagcag aggcgga    57

<210> SEQ ID NO 46
<211> LENGTH: 39
<212> TYPE: DNA
<213> ORGANISM: Artificial sequence
<220> FEATURE:
<223> OTHER INFORMATION: Description of artificial sequence : Primer - Synthetic oligonucleotide (Mutation in the FG: Y491 ---> D loop) from Mastadenovirus.

<400> SEQUENCE: 46
aaatccaaca gcgtttgtgt cggctgtgcc ttcagtaag                                    39

<210> SEQ ID NO 47
<211> LENGTH: 39
<212> TYPE: DNA
<213> ORGANISM: Artificial sequence
<220> FEATURE:
<223> OTHER INFORMATION: Description of artificial sequence : Primer -
      Synthetic oligonucleotide (Mutation in the FG: A494 ---> D loop)
      from Mastadenovirus.

<400> SEQUENCE: 47
gttaggcata aatccaacgt cgtttgtata ggctgtgcc                                    39

<210> SEQ ID NO 48
<211> LENGTH: 39
<212> TYPE: DNA
<213> ORGANISM: Artificial sequence
<220> FEATURE:
<223> OTHER INFORMATION: Description of artificial sequence : Primer -
      Synthetic oligonucleotide (Mutation in the FG: V495 ---> R loop)
      from Mastadenovirus.

<400> SEQUENCE: 48
taggttaggc ataaatcctc gagcgtttgt ataggctgt                                    39

<210> SEQ ID NO 49
<211> LENGTH: 39
<212> TYPE: DNA
<213> ORGANISM: Artificial sequence
<220> FEATURE:
<223> OTHER INFORMATION: Description of artificial sequence : Primer -
      Synthetic oligonucleotide (Mutation in the FG: G496 ---> S loop)
      from Mastadenovirus.

<400> SEQUENCE: 49
tgataggtta ggcataaatg aaacagcgtt tgtataggc                                    39

<210> SEQ ID NO 50
<211> LENGTH: 39
<212> TYPE: DNA
<213> ORGANISM: Artificial sequence
<220> FEATURE:
<223> OTHER INFORMATION: Description of artificial sequence : Primer -
      Synthetic oligonucleotide (Mutation in the FG: F497 ---> D loop)
      from Mastadenovirus.

<400> SEQUENCE: 50
agctgatagg ttaggcatgt ctccaacagc gtttgtata                                    39

<210> SEQ ID NO 51
<211> LENGTH: 39
<212> TYPE: DNA
<213> ORGANISM: Artificial sequence
<220> FEATURE:
<223> OTHER INFORMATION: Description of artificial sequence : Primer -
      Synthetic oligonucleotide (Mutation in the FG: M498 ---> D loop)
      from Mastadenovirus.

<400> SEQUENCE: 51
ataagctgat aggttagggt caaatccaac agcgtttgt                                    39

<210> SEQ ID NO 52
<211> LENGTH: 39
<212> TYPE: DNA
<213> ORGANISM: Artificial sequence
<220> FEATURE:

```
<223> OTHER INFORMATION: Description of artificial sequence : Primer -
      Synthetic oligonucleotide (Mutation in the FG: P499 ---> G loop)
      from Mastadenovirus.

<400> SEQUENCE: 52
tggataagct ataggtttc ccataaatcc aacagcgtt                                 39

<210> SEQ ID NO 53
<211> LENGTH: 39
<212> TYPE: DNA
<213> ORGANISM: Artificial sequence
<220> FEATURE:
<223> OTHER INFORMATION: Description of artificial sequence : Primer -
      Synthetic oligonucleotide (Mutation in the FG: N500 ---> D loop)
      from Mastadenovirus.

<400> SEQUENCE: 53
ttttggataa gctgataggt caggcataaa tccaacagc                                39

<210> SEQ ID NO 54
<211> LENGTH: 39
<212> TYPE: DNA
<213> ORGANISM: Artificial sequence
<220> FEATURE:
<223> OTHER INFORMATION: Description of artificial sequence : Primer -
      Synthetic oligonucleotide (Mutation in the FG: A503 ---> D loop)
      from Mastadenovirus.

<400> SEQUENCE: 54
accgtgagat tttggatagt ctgataggtt aggcataaa                                39

<210> SEQ ID NO 55
<211> LENGTH: 39
<212> TYPE: DNA
<213> ORGANISM: Artificial sequence
<220> FEATURE:
<223> OTHER INFORMATION: Description of artificial sequence : Primer -
      Synthetic oligonucleotide (Mutation in the FG: Y504 ---> D loop)
      from Mastadenovirus.

<400> SEQUENCE: 55
tttaccgtga gattttgggt cagctgatag gttaggcat                                39

<210> SEQ ID NO 56
<211> LENGTH: 39
<212> TYPE: DNA
<213> ORGANISM: Artificial sequence
<220> FEATURE:
<223> OTHER INFORMATION: Description of artificial sequence : Primer -
      Synthetic oligonucleotide (Mutation in the FG: P505 ---> G loop)
      from Mastadenovirus.

<400> SEQUENCE: 56
agttttaccg tgagattttc cataagctga taggttagg                                39

<210> SEQ ID NO 57
<211> LENGTH: 26
<212> TYPE: DNA
<213> ORGANISM: Artificial sequence
<220> FEATURE:
<223> OTHER INFORMATION: Description of artificial sequence : Primer
      from Mastadenovirus.

<400> SEQUENCE: 57
tgaaaaatga ttcgaaattt tctgca                                              26
```

MODIFIED ADENOVIRUS FIBRE AND USES

CROSS REFERENCE TO RELATED APPLICATIONS

The present application is a 371 of PCT/FR00/03263 filed Nov. 23, 2000, which claims priority to FR 9914842 filed, Nov. 25, 1999.

The present invention relates in particular to an adenoviral fiber, mutated in a region involved in recognizing and binding to the natural cellular receptor for adenoviruses. It also relates to viral particles, more particularly adenoviral particles, and to pseudoparticles, bearing such a fiber at their surface, optionally combined with a ligand which confers modified, or even targeted, host specificity on said particles and pseudoparticles. The invention is of most particular value in the context of developing vectors or compositions which can be used in the context of carrying out gene therapy protocols.

Adenoviruses have long been described as a natural system which is very effective for transferring a biological material into target cells. This is the reason why adenoviral vectors are, today, widely used in many gene therapy applications.

They have been demonstrated in many animal species and are relatively nonpathogenic, and nonintegrating, and replicate in both dividing cells and quiescent cells. In addition, they have a broad host spectrum and are capable of infecting a very large number of cell types, such as, for example, epithelial cells, endothelial cells, myocytes, hepatocytes, nerve cells and synoviocytes (Bramson et al., 1995, Curr. Op. Biotech. 6, 590-595).

The adenoviral genome consists of a double-stranded linear DNA molecule of approximately 36 kb containing two inverted repeat regions (designated ITRs for Inverted Terminal Repeat) framing the genes encoding the viral proteins. The early genes are divided into four regions dispersed in the adenoviral genome (E1 to E4; E for early), comprising six transcriptional units provided with their own promoters. The late genes (L1 to L5; L for late) cover, in part, the early transcriptional units and are, mostly, transcribed from the major late promoter, MLP.

The intracellular infectious cycle of adenoviruses is well documented in the literature and is based on two essential steps:
  (i) the early phase, which precedes replication initiation, allows the production of the early proteins which regulate replication and transcription of the viral DNA,
  (ii) the late phase, which follows replication of the genome, during which the structural proteins which constitute the basis of the viral adenoviral particles (or capsids) are synthesized.

Assembly of the new viruses then takes place in the nucleus; initially, the viral proteins assemble so as to form empty capsids of icosohedral structure, in which the newly formed genome is encapsidated. The adenoviruses released are then capable of infecting other permissive cells.

More particularly, during infection, the adenoviruses penetrate into the cells via a process of endocytosis which follows attachment of the adenoviral particle to a specific receptor present at the surface of the permissive cells. During this process, the fiber and the penton base present at the surface of the adenoviral particle play an essential role in the cellular attachment of the viruses and their internalization (Wickham et al., 1993, Cell, 73, 309-319). Specifically, the adenovirus binds to a cellular receptor (in particular CAR) present at the surface of the permissive cells, via said fiber in its trimeric form (Philipson et al., 1968, J. Virol. 2, 1064-1075; Defer et al., 1990, J. Virol. 64, 3661-3673), and then the viral particle is internalized by endocytosis via the binding of the penton base to the $\alpha_v\beta_3$ and $\alpha_v\beta_5$ cellular integrins (Mathias et al., 1994, J. Virol. 68, 6811-6814).

This natural capacity which adenoviruses have to penetrate into cells has been largely exploited in order to allow the transport of macromolecules into cells (Otero et al., 1987, Virology, 160, 75-80; Fitzgerald et al., 1983, Cell, 32, 607-617; Seth et al., 1984, Mol. Cell. Biol., 4, 1528-1533; Defer et al., 1990, J. Virol., 64, 3661-3673; Rosenfeld et al., 1991, Science, 252, 431-434; Curiel et al., 1991, Proc. Natl. Acad. Sci., 88, 8850-8854; Rosenfeld et al., 1992, Cell, 68, 143-155; Quantin et al., 1992, Proc. Natl. Acad. Sci., 89, 2581-2584; Curiel et al., 1992, Hum. Gene Therapy, 3, 147-154).

For example, besides the transfer of the adenoviral genome itself, preferably also comprising a heterologous nucleic acid sequence of interest (recombinant adenovirus), adenoviruses are capable of promoting the transfer, in vitro and in vivo, of macromolecules of nonviral origin, such as, for example, dextrans (Otero et al., 1987, Virology, 160, 75-80), proteins (Carrasco et al., 1981, Virology, 113, 623-629; Fitzgerald et al., 1983, Cell, 32, 607-617; Defer et al., 1990, J. Virol., 64, 3661-3673), a plasmid DNA associated with a ligand (Curiel et al., 1992, Hum. Gene Therapy, 3, 147-154; Cotton et al., 1992, Proc. Natl. Acad. Sci., 89, 6094-6098) optionally in the presence of an antibody which neutralizes adenoviral infection (Michael et al., 1993, J. Biol. Chem., 268, 6866-6869), of naked nucleic acids (DNA, RNA, PNA), or optionally in the presence of cationic compounds such as cationic lipids (U.S. Pat. No. 5,928,944; patent application WO 95/21259). Thus, it has been shown that the use of adenoviral particles in the context of an in vitro plasmid transfection protocol makes it possible to increase the efficiency of transfection by 100- to 1000-fold. The contents of the publications and patent applications cited above are incorporated into the present application in their entirety, by way of references.

Adenoviruses have been the subject of many studies and several scientific teams have also developed adenoviral vectors which are replication-defective, i.e. in which the genome has been manipulated such that these adenoviral vectors are incapable of dividing or proliferating in the cells which they infect. Defective adenoviral vectors are in particular obtained by deleting at least part of the E1 region (for examples of defective adenoviral vectors, see in particular patent applications WO 94/28152 and WO 94/12649).

The adenoviral fiber is composed of three distinct domains (Chroboczek et al., 1995, Current Top. Microbiol. Immunol. 199, 165-200):
  (a) at its N-terminal end, is the tail, the sequence of which is very conserved from one adenoviral serotype to the other. It interacts with the penton base and ensures the anchoring of the molecule in the capsid;
  (b) in the center, is the shaft; it is a rod-like structure composed of a certain number of sheet repeats, the number of which varies depending on the serotypes under consideration;
  (c) at its C-terminal end, is the head, which has a spherical globular structure containing the trimerization signals (Hong and Engler, 1996, J. Virol, 70, 7071-7078; Novelli and Boulanger, 1991, J. Biol. Chem. 266, 9299-9303; Novelli and Boulanger, 1991, Virology 185, 365-376) and is responsible for the binding to permissive cells (Henry et al., 1994, J. Virol. 68, 5239-5246; Louis et al., 1994, J. Virol. 68, 4104-4106). Moreover, Xia et al. (1994, Structure 2, 1259-1270) have determined the three-dimensional crystallographic structure of the adenoviral knob. Each monomer comprises 8 antiparallel sheets, designated A to D and G to J, and 6 major loops of 8 to 55 residues. For example, loop CD connects sheet C to sheet D. It is indicated that the minor sheets E and F are considered to form part of loop DG located between sheets D and G. By way of indication, table 1 indicates the location of these structures in the amino acid sequence of the Ad5 fiber, as shown in sequence identifier No. 1 (SEQ ID NO: 1), the +1 representing the initiating Met residue. In general, the sheets form an organized and compact structure, whereas the loops are more flexible. These terms are conventional in the field of protein biochemistry and are defined in fundamental works (see, for example, Stryer, Biochemistry, 2nd edition, Chap. 2, pp. 11 to 39, Ed Freeman and Company, San Francisco).

TABLE 1

| Sheets | | Loops | |
| --- | --- | --- | --- |
| Nomenclature | Residues | Nomenclature | Residues |
| A | 400 to 403 | AB | 404 to 418 |
| B | 419 to 428 | — | — |
| C | 431 to 440 | CD | 441 to 453 |
| D | 454 to 461 | DG | 462 to 514 |
| C | 515 to 521 | GH | 522 to 528 |
| H | 529 to 536 | HI | 537 to 549 |
| I | 550 to 557 | IJ | 558 to 572 |
| J | 573 to 578 | | |

The four sheets A, B, C and J constitute the V sheets directed toward the viral particle. The other four (D, G, H and I) form the R sheets, which are presumed to face the cellular receptor. The V sheets appear to play an important role in the trimerization of the structure, while the R sheets are thought to be involved in the interaction with the receptor.

Several teams have already described adenoviral particles for which the native fiber has been mutated so as to modify their natural tropism and change the binding specificity of this fiber such that it recognizes a different cellular receptor.

Thus, WO 94/10323 describes type 5 adenoviral (Ad5) particles, the fiber of which has been mutated so as to comprise the sequence of a fragment of an antibody specific for a given antigen (of scFv type) inserted at the end of one of the 22 repeat units of the shaft. The specificity of infection of the adenoviral particles thus mutated is modified in such a way that the adenoviruses produced are capable of attaching to cells which exhibit the target antigen.

U.S. Pat. No. 5,543,328 describes a chimeric adenoviral fiber in which the knob domain is replaced with the sequence of tumor necrosis factor (TNF), or that of the ApoE peptide, so as to redirect the attachment of the modified adenoviral particles to cells expressing the cellular receptor for TNF or the LDL (low-density lipoprotein) receptor, respectively.

WO 95/26412 describes a fiber modified by incorporating a ligand at its C-terminal end.

WO 96/26281 describes a chimeric fiber obtained by replacing part of the native fiber, and in particular of the knob, with the equivalent part of an adenoviral fiber from another serotype and, optionally, by inserting, at the C-terminal end, a vitronectin-specific RGD peptide.

In addition, French patent application FR 2 758 821 (97 01005) has demonstrated the role of class I major histocompatibility complex antigens and of fibronectin module 111s as, respectively, a primary receptor and a cofactor for adenoviruses. In an identical manner, Tomko et al. (1997, Proc. Natl. Acad. Sci. 94, 3352-3356), Bergelson et al. (1997, Science 275, 1320-1323) and Roelvink et al. (1998, J. Virol. 72, 7909-7915) have described another receptor for the fiber of various adenovirus serotypes. It is a 46 kDa surface molecule, CAR (Coxsackie and Adenovirus Receptor).

In application WO 98/44121, the content of which is an integral part of the present application, the inventors of the present application have already described modifications of the adenoviral fiber which are of value and which affect more particularly the domain extending from loop CD to sheet I, and more particularly extending from residues 441 to 557 of the type 5 adenovirus (Ad5) fiber (SEQ ID NO: 1) and 441 to 558 of the type 2 adenovirus (Ad2) fiber. They have, moreover, shown that, within this region, it may be advantageous to modify the part which comprises loop CD, sheet D and the proximal part of loop DG (positions 441 to 478 of the fiber of Ad2 and of Ad5) and, more particularly, the region extending from residues 443 to 462 as regards Ad5, or 451 to 466 in the case of Ad2.

More specifically, they have described the advantage of mutants of the Ad5 fiber obtained:
(i) by substitution of one or more amino acid(s) in these regions, said substitutions possibly being selected in particular from the following group:
the glycine residue at position 443 is substituted with an aspartic acid,
the serine residue at position 444 is substituted with a lysine,
the leucine residue at position 445 is substituted with a phenylalanine,
the alanine residue at position 446 is substituted with a threonine,
the serine residue at position 449 is substituted with an aspartic acid,
the glycine residue at position 450 is substituted with an asparagine or lysine,
the threonine residue at position 451 is substituted with a lysine or a leucine,
the valine residue at position 452 is substituted with an asparagine or a threonine,
the alanine residue at position 455 is substituted with a phenylalanine,
the leucine residue at position 457 is substituted with an alanine,
the isoleucine residue at position 459 is substituted with an alanine,
and/or
(ii) by deletion of all or part of said domains of the fiber, in particular of loop CD, of sheet D and/or of loop DG, and preferentially a deletion chosen from the deletions:
of the region extending from the serine at position 454 to the phenylalanine at position 461,
of the region extending from the valine at position 441 to the glutamine at position 453, or of the region extending from the valine at position 441 to the phenylalanine at position 461.

Similarly, the inventors of the present application have previously demonstrated (see patent application benefiting from the French priority No. 99/10859) the advantage provided by a modified adenovirus fiber comprising at least one mutation at one or more residues included in the region of the fiber extending from sheet. A to sheet B, and including loop AB. More particularly, mutations have been proposed which are located at one or more residues included in loop AB, in particular between residues 400 and 428, more particularly between residues 404 and 418, and preferentially between residues 404 and 408, of SEQ ID NO: 1 representing the Ad5 fiber (or equivalents defined in the sequence of the Ad2 fiber). According to a preferred case, the mutated residue is selected from the threonine residue at position 404, the alanine residue at position 406 and the serine residue at position 408. According to a particular case, the mutation produced consists of at least one substitution of an amino acid, chosen from the following substitutions:

- the serine residue at position 408 is substituted with a residue having at least two carboxyl groups, and in particular with a residue selected from the group consisting of aspartic acid and glutamic acid,
- the threonine residue at position 404 is substituted with a glycine residue,
- the alanine residue at position 406 is substituted with a lysine residue.

These two inventions produced previously by the inventors of the present invention, and the contents of which are incorporated into the present invention by way of reference, describe regions of the adenoviral fiber, and also defined mutants in said regions, which have the advantage of inhibiting or preventing binding to the natural cellular receptor for adenoviruses.

The inventors have, at the current time, identified novel mutants consisting of a modification, in particular of a substitution or a deletion, of one or more residues of the region of the adenoviral fiber between residues 491 and 505, and have shown their value for the purpose of inhibiting or preventing the infectivity of the adenoviral particles which have such a modified fiber, with respect to normally permissive cells. The aim of the present invention is, in particular, to provide a novel alternative which makes it possible to decrease the therapeutic amounts of adenoviral particles to be used and to target the infection to the cells to be treated. This specificity is particularly advantageous when an adenoviral particle expressing a cytotoxic gene is used, in order to avoid propagation of the cytotoxic effect to healthy cells. The advantages provided by the present invention are mainly those of decreasing the risks of dissemination and the side effects linked to adenoviral technology. In addition, the teachings of the present invention make it possible to set up other targeting systems intended for the development of methods of treatment by administering viral vectors, especially recombinant viral vectors, or nonviral vectors.

These novel mutants of the adenoviral fiber in particular make it possible to produce viral particles which have the following properties:

(i) the viral particle comprising said mutated fiber do not substantially attach to the natural adenoviral cellular receptors, i.e. the host specificity of these viral particles bearing the mutated fiber is reduced, or even inhibited, compared to the host specificity of the viral particles bearing the wild-type fiber, i.e. the nonmutated fiber;

(ii) when the viral particle comprising said mutated fiber also comprises a ligand specific for an anti-ligand, it is possible to confer on said modified particle a new tropism, for one or more specific cell types bearing said anti-ligand at their surface, compared to the nonmutated viral particle.

These novel mutants of the adenoviral fiber also make it possible to produce pseudoparticles, in particular viral or synthetic pseudoparticles, as described below.

The expression "the mutated fiber does not substantially attach to the natural cellular receptors" is intended to indicate that the fiber is modified so as to decrease or destroy its ability to bind to the natural cellular receptor. Such a property may be verified by studying the infectivity or the cell binding of the corresponding viral particles, by applying techniques known to those skilled in the art, and in particular through infection competition experiments for the virus bearing the modified fiber, carried out in the presence of a competitor consisting of all or part of the wild-type adenoviral fiber (for more details relating to this measuring technique, see the experimental section of the present application). The loss of the natural specificity can also be evaluated through cell attachment studies carried out in the presence of labeled viruses (for example labeled with $^3$H-thymidine according to the technique of Roelvink et al., 1996, J. Virol. 70, 7614-7621) or through studies of infectivity of permissive cells or cells expressing the surface molecule targeted by the ligand (see the examples which follow). Advantageously, "a mutated fiber does not substantially attach to the natural cellular receptors" when the percentage residual infection, measured using a competition experiment as disclosed in the examples which follow, is between approximately 0 and 60%, preferably between 0 and 40%, and entirely preferably between 0 and 20%. In addition, according to an advantageous embodiment, the properties of trimerization and of binding to the penton base of the mutated adenoviral fiber are not affected. These properties are easily verified according to the technique used in the examples which follow.

For the purpose of the invention, the terms "residues" and "amino acids" are synonyms. The terms "sheets" and "loops" are defined according to Xia et al. (1994, Structure 2, 1259-1270). The terms "virus" and "adenovirus" are synonyms of "viral particles" and "adenoviral particles", respectively. The term "particle" is intended to denote a structure comprising peptides and/or lipids, which is organized so as to consist of a capsid which may also contain a macromolecule (in particular viral genome, dextrans, proteins, nucleic acids (DNA, RNA, PNA, plasmid DNA, etc.)). The term "viral pseudoparticles" or "adenoviral pseudoparticles" is intended to denote viral or adenoviral particles which do not contain any viral or adenoviral genome, respectively (the presence of a nonviral or nonadenoviral genome not being excluded); reference may also be made, in the particular case in which no genome is present, to "empty" particles. Alternatively, the term "nonviral pseudoparticles" will denote artificial particles produced, for example, by the association of amino- or carboxy-terminal protein sequences, of peptides or glycoproteins, with lipids. Such modified lipids may then be incorporated into a liposome-type structure. Such a technique is well known to those skilled in the art and has already been applied, for example, for producing liposomes bearing surface glycoproteins of the influenza virus (Tikchonenko et al., 1988, Gene, 63, 321-330). These liposomal pseudoparticles may, of course, also comprise a macromolecule, which they transport into the target cell, and in particular a nucleic acid. The term "mutation" is intended to denote a deletion, a substitution or an addition of one or more residues, or a combination of these possibilities. According to another particular case, such a "mutation" may also consist of a modification, in particular chemical modification, of at least one residue. Such modifications in particular consist of an esterification, an alkylation, PEGylation, hydroxyalkylation, etc.

The term "nucleic acid sequence" is intended to denote a synthetic or isolated natural, linear or circular, double-stranded or single-stranded fragment of DNA and/or of RNA and/or of PNA denoting a precise series of nucleotides, which may or may not be modified, making it possible to define a fragment or a region of a nucleic acid without size limitation. According to a preferred embodiment, it is a nucleic acid chosen from the group consisting of a cDNA (complementary DNA); a genomic DNA; a plasmid DNA; an RNA and a viral genome.

The term "part" of an amino acid sequence is intended to mean an amino acid sequence comprising a minimum of 6 consecutive amino acids, preferably 10, more preferably 15, even more preferably 20, and most preferably 30, and/or having the same biological activity as the sequence from which said part is derived, in particular the ability to recognize and to bind to the target cells of the virus.

The term "part" of a nucleic acid sequence is intended to mean a nucleic acid sequence comprising a minimum of 18 consecutive nucleotides, preferably 30, more preferably 45, even more preferably 60, most preferably 90, and/or encoding an amino acid sequence having the same biological activity as the amino acid sequence encoded by the nucleic acid sequence from which said part is derived.

The expression "elements which ensure the expression of said gene in vivo" is intended to denote the elements required in order to ensure expression of said gene after it has been transferred into a target cell. They are in particular promoter sequences and/or regulatory sequences which are effective in said cell and, optionally, the sequences required to allow expression of said polypeptide at the target cell surface. The promoter used may be a viral, ubiquitous or tissue-specific promoter, or a synthetic promoter. By way of example, mention will be made of promoters such as the promoters of the RSV (Rous Sarcoma Virus), MPSV, SV40 (Simian Virus) or CMV (Cytomegalovirus) viruses or of the vaccinia virus, or the promoters of the gene encoding muscle creatine kinase, actin or pulmonary surfactant. It is also possible to choose a promoter sequence which is specific for a given cell type or which can be activated under defined conditions (see, for example, U.S. Pat. No. 5,874,534). The literature provides a great deal of information relating to such promoter sequences. According to a preferred case, said "nucleic acid sequence" also contains a "heterologous" gene, i.e. a gene the origin of which is different from that of the nucleic acid sequence which contains it. Examples of such genes are indicated below. Moreover, said nucleic acid sequence may comprise at least two sequences, which may be identical or different, having transcriptional promoter activity, and/or at least two genes, which may be identical or different, located contiguously with respect to one another, at a distance from one another, in the same direction as one another or in opposite directions to one another, provided that the transcriptional promoter function or the transcription of said genes is not affected. Similarly, it is possible to introduce, into this type of nucleic acid construct, "neutral" nucleic acid sequences, or introns, which do not hinder the transcription and are spliced before the translation step. Such sequences and the uses thereof are described in the literature (WO 94/29471). Said nucleic acid may also contain sequences required for intracellular transport, for replication and/or integration, for transcription or for translation. Such sequences are well known to those skilled in the art. Moreover, the nucleic acids which can be used according to the present invention may also be nucleic acids modified such that it is impossible for them to integrate into the genome of the target cell, or nucleic acids stabilized using agents, such as for example spermine, which, as such, have no effect on the efficiency of introduction of the nucleic acid into the cells.

The fiber according to the present invention may be derived from an adenovirus of human, canine, avian, bovine, murine, ovine, porcine or simian origin, or may comprise fragments of diverse origins, including fragments of heterologous origin, i.e. fragments not derived from an adenoviral fiber or derived from nonadenoviral fibers (this is then preferentially described as a "hybrid fiber"). With regard to the human adenoviral fiber, reference is preferably made to that derived from serotype C, and in particular derived from the type 2 or 5 adenovirus (Ad2 or Ad5). The Ad2 fiber comprises 580 amino acids (aa), the sequence of which is disclosed in Herisse et al. (1981, Nucleic Acid Res. 9, 4023-4042), the content of which is incorporated into the present application by way of reference. That of Ad5 has been determined by Chroboczek and Jacrot (1987, Virology 161, 549-554) and has 582 amino acids (SEQ ID NO: 1). In order to simplify the explanation of the present application, only the positions relating to Ad5 are given. However, it is within the scope of those skilled in the art to identify the equivalent positions of the various sheets and loops on the basis of the sequences of adenoviral fibers of other origins (this constituting an embodiment equivalent to that detailed in the present application). For example, those skilled in the art can identify the adenoviral fiber sequences available on the databases such as GenBank and determine the equivalent positions of the various sheets and loops and residue positions as described previously. By way of information, mention is in particular made of the GenBank references for the sequences of the adenoviral fiber of human serotype 2 (# AAA92223), 3 (# CAA26029), (# M18369), 31 (# CAA54050) or 41 (# X17016). When the fiber of the present invention is of animal origin, use is preferably made of bovine adenoviruses, and in particular those of the BAV-3 strain. The latter have been the subject of many studies, and the sequence of the fiber is disclosed in application WO 95/16048. Of course, the fiber of the present invention may, besides the modifications described in the present invention, have other modifications relative to the native sequence, as long as they do not affect the characteristics of the fibers provided in the application. The contents of the publications or of the GenBank references cited above are incorporated into the present application in their entirety, by way of reference. The invention also relates to a modified fiber as described in the present application, which also contains other mutations, such as, for example, those described in patent application WO 98/44121 or in the patent application benefiting from the French priority No. 99/10859 (see above in the present application).

It should be specified that, according to the invention, the region of the Ad5 adenoviral fiber between residues 491 and 505, and modified as described in the present application, may, of course, be introduced into the heterologous adenoviral fiber, i.e. a fiber which is different from the Ad5 adenoviral fiber, as an addition to, or as a substitution for, the equivalent region of said heterologous fiber.

According to a first embodiment, the invention relates to an adenovirus fiber which is modified by mutation of one or more residues of the region between residues 491 and 505 of SEQ ID NO: 1. Preferentially, it is an adenoviral fiber comprising all or part of the sequence of the type 5 adenovirus (Ad5) fiber as shown in sequence identifier No. 1 (SEQ ID NO: 1) and modified by mutation of one or more residues of the region between residues 491 and 505 of said sequence.

As indicated above, according to a variant, the mutation may be produced by substitution of one or more amino acids in the regions stated. In this capacity, mention may be made of the following examples, according to which the Ad5 fiber bears at least one mutation chosen from the following mutations:

the tyrosine residue at position 491 is substituted with an aspartic acid, the alanine residue at position 494 is substituted with an aspartic acid, the valine residue at position 495 is substituted with an arginine, the glycine residue at position 496 is substituted with a serine, the phenylalanine residue at position 497 is substituted with an aspartic acid, the methionine residue at position 498 is substituted with an aspartic acid, the proline residue at position 499 is substituted with a glycine, the asparagine residue at position 500 is substituted with an aspartic acid, the alanine residue at position 503 is substituted with an aspartic acid, the tyrosine residue at position 504 is substituted with an aspartic acid, the proline residue at position 505 is substituted with a glycine.

The invention preferably relates to a type 5 adenovirus fiber, characterized in that the mutated residue is selected from the alanine residue at position 494 and the alanine residue at position 503.

Due to their spatial localization in the native fiber, these residues are capable of recognizing and/or interacting directly or indirectly with the natural cellular receptor for the adenovirus concerned.

According to a particular embodiment, a fiber according to the invention is characterized in that it comprises, besides the modifications described above, one or more mutations in:

loops AB, CD, DG, GH, HI and/or IJ and/or sheets A, B, C, D, G, H, I and/or J, and, more particularly, one or more mutations as described previously by the applicant in application WO 98/44121 and the patent application benefiting from the French priority No. 99/10859 (see also above).

In accordance with the invention, it is preferable not to drastically modify the three-dimensional structure of the adenoviral fiber; thus, the amino acids forming a bend will be replaced with residues forming a similar structure, such as those cited in Xia et al. 1994.

The fiber of the present invention may also be modified by deletion.

According to an advantageous embodiment, when at least one of the modifications is a deletion of at least 3 consecutive residues of a loop and/or of a sheet, the deleted residues may be replaced with residues from an equivalent loop and/or sheet derived from a fiber of a second adenovirus capable of interacting with a cellular receptor different from that recognized by the first adenovirus. This makes it possible to maintain the structure of the fiber according to the invention while at the same time conferring on it a host specificity corresponding to that of the second adenovirus. As indicated in Xia et al. (1994), the region of the fiber which is involved during infection and interacts with the cellular receptor is different for the type 3 and 7 adenoviruses. Thus, an Ad5 or Ad2 fiber deleted of at least 3 consecutive residues from those specified above perhaps substituted with the residues derived from an equivalent region of the Ad3 or Ad7 fiber so as to decrease its ability to bind the receptor for Ad5 and thus confer on it a new specificity toward the cellular receptor for Ad3 or for Ad7.

The present invention also relates to an adenovirus fiber having a substantially decreased ability to bind to the natural cellular receptor, as shown above, but nevertheless capable of trimerization. Such a property is in particular determined using the technique described in the experimental section of the application.

According to an equally advantageous embodiment, the fiber according to the invention also comprises a ligand, or targeting element. For the purpose of the present invention, the term "ligand" defines any entity capable of recognizing and binding to or interacting with, preferably with high affinity, a cellular "anti-ligand" which is different from the natural cellular receptor for the nonmutated adenoviral fiber (i.e. antigens of the class I histocompatibility system, fibronectin or the cellular receptor for the coxsackie virus (CAR)). This anti-ligand may be expressed or exposed at the surface of the cell the targeting of which is desired (cell surface marker, receptor, antigenic peptide presented by histocompatibility antigens, etc.), naturally or subsequent to a modification of said target cell aimed at making it express or expose such an anti-ligand at its surface. In accordance with the aims pursued by the present invention, such a ligand may, for example, be an antibody or an antibody fragment, a lipid, a glycolipid, a hormone, a polypeptide, a short peptide, a polymer (PEG, polylysine, PEI, etc.), a sugar, an oligonucleotide, an antigen, a vitamin, all or part of a lectin or the peptide JTS-1 (WO 94/40958), or a combination of such compounds. The term "antibody" in particular denotes monoclonal antibodies, antibody fragments (such as, for example, a Fab fragment) and single-chain antibodies (scFv). These names and abbreviations are conventional in the field of immunology. Moreover, such targeting elements make it possible to direct the particle or pseudoparticle to certain cell types or certain particular tissues (tumor cells, pulmonary epithelium cells, hematopoietic cells, muscle cells, nerve cells, etc.). They may also be elements which facilitate penetration into the cell or, optionally, endosomal lysis. In particular, they may be galactosyl residues which make it possible to target the receptor for asialoglycoproteins at the surface of hepatic cells, ligands which can interact with receptors, such as receptors for growth factors, receptors for cytokines, lectins, or adhesion proteins; they may also be an antibody fragment, such as the Fab fragment, a fusogenic peptide INF-7 derived from the HA-2 subunit of influenza virus hemagglutinin (Plank et al., 1994, J. Biol. Chem. 269, 12918-12924), a nuclear localization signal derived from the SV40 virus T antigen or from the Epstein Barr virus EBNA-1 protein, the GRP (Gastrin Releasing Peptide) ligand, the EPPT peptide (U.S. Pat. No. 5,591,593) or the LDV peptide (U.S. Pat. No. 5,628,979).

In the context of the present invention, it may be advantageous to target more particularly a tumor cell, an infected cell, a specific cell type or a category of cells bearing a specific surface marker. For example, if the host cell to be targeted is a cell infected with the HIV virus (Human Immunodeficiency Virus), the ligand may be a fragment of an antibody directed against fusin, the CD4 receptor or a viral protein (envelope glycoprotein) or the part of the HIV virus TAT protein which extends from residue 37 to 72 (Fawell et al., 1994, Proc. Natl. Acad. Sci. USA 91, 664-668). As regards a tumor cell, the choice will relate to a ligand which recognizes an antigen which is tumor-specific (for example the MUC-1 protein in the case of breast cancer, certain epitopes of the HPV papillomavirus E6 or E7 proteins) or which is overexpressed (IL-2 receptor overexpressed in certain lymphoid tumors). If the intention is to target T lymphocytes, a ligand for the T cell receptor may be used. Moreover, transferrin is a good candidate for hepatic targeting. In general, the ligands which may be used in the context of the invention are widely described in the literature and the genes encoding such ligands may be cloned using standard techniques (for example by cDNA amplification, etc.). It is also possible to synthesize them chemically and to couple them to the modified fiber according to the invention. In this respect, coupling of galactosyl residues makes it possible to confer hepatic specificity due to the interaction with asialoglycoprotein receptors. Finally, according to a preferred embodiment, said ligand is inserted at the C-terminal end of the fiber according to the invention, or as a replacement for the residues deleted when at least one of the modifications is a deletion of at least 3 consecutive residues.

Depending in particular on the chemical nature of the ligand, it may be incorporated into the modified fiber according to the invention in different ways, and more particularly:

by cloning the nucleic acid sequence encoding said ligand into the nucleic acid sequence encoding the modified fiber of interest. In this regard, preference will be given to the particular case according to which said nucleic acid sequence encoding the ligand is introduced into or close to the region of the nucleic acid sequence of the fiber encoding the mutated region of said fiber;

by incorporation directly onto the fiber modified and produced beforehand, for example by chemical grafting.

Another subject of the invention relates to a peptide fragment, characterized in that it comprises the region extending from residue 491 to residue 505 of SEQ ID NO: 1, and in that said region is modified as described above.

Such a peptide fragment in particular has the following properties:

(i) when this peptide fragment is incorporated in place of a region extending from residues 491 to 505 of SEQ ID NO: 1 of a given adenoviral fiber (or in equivalent positions), the adenoviral particle comprising said modified fiber does not substantially attach to the natural cellular receptors for the unmodified adenoviral fiber;

(ii) when the adenoviral particle comprising said mutated fiber according to (i) also comprises a ligand specific for an anti-ligand, it is possible to confer on said modified adenoviral particle a new tropism, for one or more specific cell types bearing at their surface a said anti-ligand, compared to the adenoviral particle comprising said unmodified adenoviral fiber.

The present invention also relates to a viral particle, in particular an adenoviral particle, which comprises, at its surface, a modified fiber or a peptide according to the invention and, optionally, a ligand as defined above. According to a preferred case, this viral particle lacks a functional native fiber or any other peptide naturally involved in the attachment of said viral particle to its target cell.

When such a particle contains a viral genome, reference is preferentially made to a "viral virus" and, in the particular case according to which said genome is also modified, reference will more especially be made to a "recombinant viral virus" (for example a recombinant adenovirus, and preferentially a replication-defective recombinant adenovirus). Such cases are described in greater detail below. The invention therefore also relates to such viruses and recombinant viruses.

In order to obtain viral particles, in particular adenoviral particles, according to the invention, the modified fiber or said peptide and, optionally, said ligand:

(i) may be expressed by the viral genome itself, in particular when said viral particle at the end contains such a genome. In this case, said genome contains the nucleic acid sequences required for the expression of said modified fiber or for a said peptide according to the invention and, optionally, for a said ligand;

(ii) may be provided in trans by a complementation cell line, as defined below, which contains the nucleic acid sequences required for the expression of said modified fiber or for a said peptide according to the invention and, optionally, for a said ligand;

(iii) may be incorporated at the surface of said viral particle by chemical modification, more particularly after the production of viral particles according to techniques widely used by those skilled in the art who specialize in viral production. According to a particular case, according to (iii), said viral particles are not adenoviral particles, and are preferentially nonenveloped viral particles. Such viruses are widely described in general works on virology, such as, for example, Fields et al. (1990, Virology, Raven Press, NY).

According to a particular embodiment, the viral particle of the invention is as presented above and is characterized in that said ligand is inserted into a protein of the viral capsid other than the fiber, in particular the hexon or the penton in the precise case of adenoviral particles. According to an advantageous embodiment, said viral genomes and particles are adenoviral genomes and particles.

The invention also relates to a viral pseudoparticle, in particular an adenoviral pseudoparticle, which comprises, at its surface, a mutated fiber or a peptide according to the invention and, optionally, a ligand as defined above. According to a particular case of the invention, said viral pseudoparticle of the invention is "empty", i.e. it does not contain any nucleic acid. However, the invention also relates to the cases for which such a viral pseudoparticle contains a macromolecule, and more particularly a nucleic acid which is not a viral or adenoviral genome. The use of such viral pseudoparticles is in particular illustrated in document WO 95/21259 or U.S. Pat. No. 5,928,944 mentioned above.

According to another embodiment, the invention also relates to pseudoparticles which may also be designated "artificial particles". Such particles may in particular be produced after (i) formation of polar compounds such as lipids or glycolipids associated with amino- or carboxy-terminal protein sequences of peptides or glycoproteins containing or consisting of the peptide sequences or the modified adenoviral fiber according to the invention, and (ii) incorporation of said modified polar compounds into a liposome-type structure.

Such a technique is well known to those skilled in the art and has already been applied, for example, for producing liposomes bearing the surface glycoproteins of the influenza virus (Tikchonenko et al., 1988, Gene, 63, 321-330).

According to another particular case of the invention, said pseudoparticle is produced after (i) formation of polar compounds such as lipids or glycolipids associated with amino- or carboxy-terminal protein sequences of peptides or glycoproteins containing or consisting of the peptide sequences or the modified adenoviral fiber as described in application WO 98/44121 or the patent application benefiting from the French priority No. 99/10859 (see also above), and (ii) incorporation of said modified polar compounds into a liposome-type structure.

It is also possible to obtain cationic lipids or polymers modified so as to comprise such sequences or said modified adenoviral fiber in their structure. The literature provides a large number of examples of lipids which can be used according to the invention. Mention may also be made of the case of cationic lipids or polymers generally used as synthetic vectors for transferring nucleic acid into cells by transfection. By way of nonlimiting illustration, they may be compounds such as those described in Felgner et al., 1987, Proc. West. Pharmacol. Soc. 32, 115-121; Hodgson and Solaiman, 1996, Nature Biotechnology 14, 339-342; Remy et al., 1994, Bioconjugate Chemistry 5, pp. 647-654 or in patent applications WO 98/08489, WO 98/17693, WO 98/34910, WO 98/37916, WO 98/53853, EP 890362 or WO 99/05183. These cationic compounds are capable of forming complexes (also called lipoplexes or polyplexes, or more generally posiplexes) with nucleic acids in order to allow their introduction into cells (transfection). The incorporation of such peptide sequences or of a modified adenoviral fiber according to the invention into said complexes makes it possible, for example, to obtain posiplexes capable of targeting a cell type of interest.

When a ligand is also included in the particle or pseudoparticle (viral or artificial), it may be chemically coupled thereto. However, preference will be given to the variant according to which the sequences encoding the ligand are inserted into the viral genome, and preferentially adenoviral genome. In these cases, said sequences are preferentially inserted into the sequences encoding the modified fiber according to the invention, and more specifically inserted in phase in order to preserve the reading frame. Insertion of the sequence encoding the ligand may take place at any site in the viral genome; however, the preferred site of insertion is upstream of the stop codon at the C-terminal end or in place of the deleted residues. It is also possible to envision introducing the sequences of the ligand into other viral sequences, in particular those encoding another capsid protein, such as the adenoviral hexon or penton.

Advantageously, the invention relates to adenoviral particles containing a replication-defective recombinant adenovirus, i.e. an adenovirus incapable of replicating autonomously in a host cell. The deficiency is obtained by mutation or deletion of one or more essential viral genes and, in particular, of all or part of the E1 region in the adenoviral genome. Deletions within the E3 region may be envisioned in order to increase cloning capacities. However, it may be advantageous to conserve the sequences encoding the gp19k protein (Gooding and Wood, 1990, Critical Reviews of Immunology 10, 53-71) in order to modulate the host's immune response. Of course, the genome of an adenovirus according to the invention may also comprise additional deletions or mutations which affect other regions, in particular the E2, E4 and/or L1-L5 regions (see, for example, WO 94/28152 or WO 94/12649, or Ensinger et al., 1972, J. Virol. 10, 328-339, describing the heat-sensitive mutation of the DBP gene of E2).

According to a preferred embodiment, a recombinant virus (especially a recombinant adenovirus) of the invention comprises one or more gene(s) of interest placed under the control of the elements required for its (their) expression in a host cell. The gene in question may be of any origin, genomic, cDNA (complementary DNA) or hybrid (minigene lacking one or more introns). It may be obtained using the conventional molecular biology techniques, or by chemical synthesis. It may encode an antisense RNA, a ribozyme or an mRNA which will then be translated into a polypeptide of interest. This polypeptide may be cytoplasmic, nuclear or membrane-bound, or may be secreted by the host cell. Moreover, it may be all or part of a polypeptide as found naturally, of a chimeric polypeptide originating from the fusion of sequences of diverse origins, or of a polypeptide which is mutated relative to the native sequence and has improved and/or modified biological properties.

In the context of the present invention, it may be advantageous to use the genes encoding the following polypeptides:
cytokines or lymphokines (interferons and interleukins, and in particular IL-2, IL-6, IL-10 or IL-12, tumor necrosis factors (TNFs), colony stimulating factors (GM-CSF, C-CSF, M-CSF, etc.);
cellular or nuclear receptors, in particular those recognized by pathogenic organisms (viruses, bacteria or parasites) and, preferably, by the HIV virus, or the ligands thereof;
proteins involved in a genetic disease (factor VII, factor VIII, factor IX, dystrophin or minidystrophin, insulin, CFTR (Cystic Fibrosis Transmembrane Conductance Regulator) protein, growth hormones (hGH);
enzymes (urease, renin, thrombin, etc.);
enzyme inhibitors (1-antitrypsin, antithrombin III, viral protease inhibitors, etc.);
polypeptides with an antitumor effect which are capable of inhibiting, at least partially, the initiation or the progression of tumors or cancers (antibodies, inhibitors which act on cell division or on transduction signals, expression products of tumor suppressor genes, for example p53 or Rb, proteins which stimulate the immune system, etc.);
class I or II major histocompatibility complex proteins or regulatory proteins which act on the expression of the corresponding genes;
polypeptides capable of inhibiting a viral, bacterial or parasitic infection or the development thereof (antigenic polypeptides having immunogenic properties, antigenic epitopes, antibodies, transdominant variants capable of inhibiting the action of a native protein by competition, etc.);
toxins (thymidine kinase of herpes simplex virus 1 (TK-HSV-1), ricin, cholera toxin, diphtheria toxin, etc.) or immunotoxins; and
markers ($\beta$-galactosidase, luciferase, etc.)
all or part of an antibody, in particular of a monoclonal antibody.

It should be pointed out that this list is not limiting and that other genes may also be used.

Moreover, a recombinant adenovirus according to the invention may also comprise a gene for selection which makes it possible to select or identify the infected cells. Mention may be made of the neo gene (encoding neomycin phosphotransferase) which confers resistance to the antibiotic G418, the dhfr (Dihydrofolate Reductase) gene, the CAT (Chloramphenicol Acetyl transferase) gene, the pac (Puromycin Acetyl transferase) gene or the gpt (Xanthine-Guanine Phosphoribosyl transferase) gene. In general, the genes for selection are known to those skilled in the art.

The expression "elements required for the expression of a gene of interest in a host cell" is intended to mean all of the elements which allow its transcription to RNA and the translation of an mRNA to protein. Among these, the promoter is of particular importance. In the context of the present invention, it may originate from any gene of eukaryotic or even viral origin and may be constitutive or regulatable. Moreover, it may be modified so as to improve the promoter activity, suppress a transcription-inhibiting region, make a constitutive promoter regulatable or vice versa, introduce a restriction site, etc. Alternatively, it may be the natural promoter of the gene to be expressed. By way of examples, mention may be made of the CMV (Cytomegalovirus), RSV (Rous Sarcoma Virus), HSV-1 virus TK gene, SV40 virus (Simian Virus 40) early, and MLP adenoviral viral promoters, or the eukaryotic promoters of the murine or human PGK (Phosphoglycerate kinase) 1-antitrypsin (liver-specific) and immunoglobulin (lymphocyte-specific) genes.

Of course, a gene of interest used in the present invention may also comprise additional elements required for expression (intron sequence, signal sequence, nuclear localization sequence, transcription-terminating sequence, translation initiation site of the IRES or other type, etc.) or for its persistence in the host cell. Such elements are known to those skilled in the art.

However, the invention also relates to viral particles for which the genome incorporated is not an adenoviral genome. In this case, the viral genome is preferentially selected from the viral genomes corresponding to nonenveloped viruses (Fields et al., 1990, Virology, Raven Press, NY). According to this particular embodiment, the modified fiber or the peptide sequence of the invention may be incorporated into the particle either
(i) by cloning the corresponding nucleic acid sequence into the viral genome in question (expression of a fusion protein for example),
(ii) by modifying the particle naturally obtained in the context of the production of the virus in question (for example by chemical post-grafting) or alternatively
(iii) by modifying the viral genome such that it possesses the signals required for its encapsidation (psi sequence, etc.) in a particle of adenoviral origin comprising said modified fiber of the invention (complementation cell line producing the recombined proteins of the adenoviral capsid and use of a helper vector).

The present invention also relates to a DNA fragment encoding a fiber or a peptide fragment according to the invention, and also to an expression vector comprising such a DNA fragment. Any type of vector may be used for this purpose, whether it is of plasmid or viral origin, integrative or nonintegrative. Such vectors are commercially available or described in the literature. Similarly, those skilled in the art are capable of adapting the regulatory elements required for the expression of the DNA fragment according to the invention. According to a particular case of the invention, a said vector will be an adenoviral vector capable of producing, under suitable culturing conditions, adenoviral particles according to the invention, namely adenoviruses or recombinant adenoviruses as described above.

The invention also relates to a method for preparing adenoviral pseudoparticles according to the invention, according to which:
(i) the adenoviral genome encoding a modified fiber according to the invention is transfected into a suitable cell line, for example the 293 line or PERC6 line, or a derived or equivalent line;
(ii) said transfected cell line is cultured cultured under suitable conditions so as to allow the production of said adenovirus or said recombinant adenovirus, and
(iii) the empty pseudoparticles are recovered by purifying the cell lysate on a density gradient, in particular a cesium chloride gradient for example.

The empty pseudoparticles sediment, for example, at 1.3 g/ml of cesium chloride, whereas the recombinant adenoviruses (particles containing the adenoviral genome) sediment, themselves, at 1.34 g/ml (D'Hallivin, 1995, Cur. Top. Microbiol. Immunol, 199, 47-66).

According to another method, it is possible to obtain empty pseudoparticles after transfecting an adenoviral genome, carrying a modified encapsidation sequence and also containing a DNA fragment encoding a modified fiber according to the invention, into suitable cells. Modification of the encapsidation region makes it possible to decrease, or even eliminate, the phenomenon of encapsidation of the adenoviral genome into the particles (Grable and Hearing, 1992, J. Virol, 66, 723-731). The production steps which follow the culturing are identical to those described above.

The invention also relates to a method for preparing an adenovirus or a recombinant adenovirus (adenoviral particles or recombinant adenoviral particles) according to the invention, according to which:
(i) the genome of said adenovirus, which may or may not be recombinant and which may or may not be replication-defective, is transfected into a suitable cell line (293, PERC6, or derived or equivalent lines),
(ii) said transfected cell line is cultured under suitable conditions so as to allow the production of said adenovirus or of said recombinant adenovirus (it is also possible to refer to adenoviral particles) and
(iii) said adenovirus or said recombinant adenovirus is recovered from the culture of said transfected cell line and, optionally,
(iv) said adenovirus is purified.

The choice of cell line depends, where appropriate, on the deficient functions of the adenovirus according to the invention. A complementation line capable of providing the defective function(s), in trans, will in particular be used. The 293 (ATCC CRL1573) or PERC6 (ECACC 96022940) lines are most particularly suitable for complementing the E1 function (Graham et al., 1977, J. Gen. Virol. 36, 59-72 or WO 97/00326, respectively).

For an E1 and E2 or E4 double deficiency, a line among those described in French patent application FR 2737222 (96/04413) may be used. It is also possible to use an auxiliary virus to complement the defective adenovirus according to the invention in any host cell, or a mixed system using a complementation cell and an auxiliary virus, in which the elements are dependent upon one another. The means for propagating a defective adenovirus are known to those skilled in the art, who can refer, for example, to Graham and Prevec, 1991, Methods in Molecular Biology, vol. 7, pp. 190-128; Ed. E J Murey, The Human Press Inc. The adenoviral genome is preferably reconstituted in vitro in *Escherichia coli* (*E coli*) by ligation or homologous recombination (see, for example, French application FR 2727689 (94/14470)). The purification methods are described in the state of the art. Mention may be made of the density gradient centrifugation technique.

The present invention also relates to a cell line comprising, either in a form integrated into the genome or in the form of an episome, a DNA fragment encoding a fiber according to the invention placed under the control of the elements which allow its expression. Said line may derive from a cell which complements one or more adenoviral functions selected from those encoded by the E1, E2, E4 and L1-L5 regions. It preferably derives from the 293 line or from the PERC6 line. Such a line may be useful for preparing an adenovirus, in particular a recombinant adenovirus, the genome of which lacks all or part of the sequences encoding the fiber (so as to produce a nonfunctional or "redirected" fiber, or so as not to produce a fiber).

For this reason, the invention also relates to a method for producing adenoviral particles containing an adenoviral genome lacking all or part of the sequences encoding a fiber, characterized in that:
(i) said genome is transfected into a cell line given above,
(ii) said transfected cell line is cultured under suitable conditions so as to allow the production of said adenoviral particle, and
(iii) said adenoviral particle is recovered from the culture of said transfected cell line and, optionally,
(iv) said adenoviral particle is purified.

The present invention also covers a host cell which can be infected with an adenovirus according to the invention or which can be obtained using a method according to the invention. It is advantageously a mammalian cell, and in particular a human cell. It may be a primary cell or a tumor cell and may be of any origin, for example hematopoietic (totipotent stem cell, leukocyte, lymphocyte, monocyte or macrophage, etc.), muscle, nasal, pulmonary, tracheal, hepatic, epithelial, retinal (for example HER, for Human Embryonic retinocyte) or fibroblast origin.

A subject of the invention is also a composition comprising, as a therapeutic or prophylactic agent, a host cell, a viral particle, in particular an adenoviral particle, or a pseudoparticle (viral or artificial), according to the invention or which can be obtained using a method according to the invention, in combination with a pharmaceutically acceptable support. The composition according to the invention is, in particular, intended for the preventive or curative treatment of diseases such as genetic diseases, (hemophilia, cystic fibrosis, diabetes or Duchenne myopathy, Becker myopathy, etc.), cancers, such as those induced by oncogenes or viruses, viral diseases, such as hepatitis B or C and AIDS (acquired immunodeficiency syndrome resulting from infection with HIV), and recurring viral diseases, such as viral infections caused by the herpesvirus.

According to a particular embodiment, and as described in U.S. Pat. No. 5,928,944, the composition containing a viral particle, in particular an adenoviral particle, or a viral or artificial pseudoparticle of the invention also comprises a nucleic acid and a cationic substance, such as, for example, monocationic lipids (for example DOTMA, lipofectin, DOTAP, DOPE, etc.), polycationic lipids (DOGS, tTransfectam, Lipofectamine, etc.), cholesterol or derivatives thereof, phospholipids, polycarbenes (polybrene, etc.), carbohydrates (DEAE-dextran, polyamino acids, etc.), cationic polymers, etc. It may also comprise neutral or uncharged lipids. Preferably, said nucleic acid contains one or more gene(s) of interest placed under the control of the elements required for its (their) expression in a host cell and/or a selectable marker as described above.

A composition according to the invention may be produced conventionally. In particular, the therapeutic or prophylactic agent is combined with a pharmaceutically acceptable support or diluent. Such a support or such a diluent is nontoxic for the patient. It may be an injectable solution, an isotonic solution, the pH of which is compatible with use in vivo, or a solution of dextrose, of glycerol, of mannitol, and the like, and also containing, optionally, pharmacologically compatible dispersing agents and/or wetting agents.

A composition according to the invention may be administered locally, systemically or by aerosol, in particular via the intragastric, subcutaneous, intracardiac, intramuscular, intravenous, intraperitoneal, intratumoral, intrapulmonary, intranasal or intratracheal route. The administration may take place in a single dose or in a dose repeated one or more times after a certain period of delay. The suitable route of administration and dose vary depending on various parameters, for example, on the individual or on the disease to be treated, or on the gene(s) of interest to be transferred. In particular, the viral particles according to the invention may be formulated in the form of doses of between $10^4$ and $10^{14}$ pfu (plaque-forming units), advantageously $10^5$ and $10^{13}$ pfu and preferably $10^6$ and $10^{12}$ pfu. The formulation may also include a pharmaceutically acceptable adjuvant or excipient. The composition according to the invention may also be formulated in the form of a solid or semi-solid preparation, in particular in the form of a gas, tablet, capsule, powder, gelatin capsule, granule, cream, solution, suppository or aerosol, depending on the route of administration selected.

In the pharmaceutical compositions of the present invention, the active ingredient may be formulated with conventional pharmaceutical supports known to those skilled in the art.

These supports in particular comprise a pharmaceutical vehicle such as gelatin, starch, lactose, magnesium stearate, talc, sucrose, gum arabic or the like.

It is also possible to obtain a preparation of gelatin capsules by mixing the active ingredient with a diluent and pouring the mixture obtained into soft or hard gelatin capsules.

A preparation in the form of a syrup or of an elixir may contain the active ingredient together with a sweetener, an antiseptic and also a flavoring and a suitable coloring.

The water-dispersible powders or granules may contain the active ingredient as a mixture with dispersing agents or wetting agents, or suspending agents, and also with flavor enhancers or sweeteners.

For rectal administration, use is made of suppositories which are prepared with binders which melt at rectal temperature, for example cocoa butter or polyethylene glycols.

The active principle may also be formulated in the form of microcapsules, optionally with one or more additive supports.

With a view to their use for promoting the introduction of macromolecules (in particular nucleic acids) into cells, the viral particles, in particular adenoviral particles, or the pseudoparticles according to the invention may also be complexed or combined with synthetic or natural compounds, as described in the section introducing the present application, in O'Riordan et al., (1999, Human Gene Therapy, 10, 1349-1358) or in patent application WO 98/44143 or U.S. Pat. No. 5,928,944. The content of these documents is incorporated into the present invention by way of reference.

Finally, the present invention relates to the use of a peptide fragment, of a modified adenoviral fiber, of a viral particle, in particular an adenoviral particle, of a pseudoparticle or of a host cell according to the invention, or of an adenovirus which can be obtained using a method according to the invention, for preparing a medicinal product intended for treating the human or animal body. According to a first possibility, the medicinal product may be administered directly in vivo (for example by intravenous injection, into an accessible tumor, into the lungs by aerosol, etc.). It is also possible to adopt the ex vivo approach, which consists in removing cells from the patient (bone marrow stem cells, peripheral blood lymphocytes, muscle cells, etc.), transfecting or infecting them in vitro according to techniques known to those skilled in the art, and readministering them to the patient.

The invention also extends to a treatment method according to which a therapeutically effective amount of an adenovirus or of a host cell or of a pharmaceutical composition according to the invention is administered to a patient who needs such a treatment. Such a therapeutically effective amount is such that it makes it possible to observe, in the organism treated, a desired effect which may be monitored using various techniques known to those skilled in the art. For example, a desired effect may consist of the transfer of a nucleic acid into the target cells of the host. Such a transfer may be evaluated using any method which demonstrates either said transfer or the expression of a gene encoded by said nucleic acid (by polymerized chain reaction, PCR, by Northern or Southern hybridization analyses, by immunodetection of the peptide encoded, etc.). Those skilled in the art are capable of making the adjustments necessary to determine the most suitable therapeutically effective amount.

More generally, the invention relates to the use of a peptide fragment, of a modified adenoviral fiber, of a viral particle, in particular an adenoviral particle, of a pseudoparticle or of a host cell according to the invention, or of an adenovirus which can be obtained using a method according to the invention, to allow the transfer of a nucleic acid (plasmid, DNA, RNA, PNA, viral genome, etc.) of interest into target cells, in vivo or in vitro.

According to another embodiment, the invention relates to antibodies specifically directed against a modified adenoviral fiber according to the invention. Such antibodies, and most particularly monoclonal antibodies, are easily obtained by immunizing immunocompetent animals with the peptide sequences or the modified fibers according to the invention, in accordance with usual practices in the field of antibody production using an identified peptide or polypeptide. Such antibodies, and in particular specific antibodies, may be useful for carrying out, for example, monitoring of the treatment of patients to whom the particles or pseudoparticles of the invention are administered. They may also be used for preparing a composition intended to be administered in vivo to the patient treated with the particles or pseudoparticles of the invention, in order to allow said treatment to be interrupted. A said antibody may also be modified to enable it to be detected, for example by incorporating a label or an enzyme capable of reacting with a substrate, in particular a chromogenic substrate. Such applications are well known in the diagnostic field.

EXAMPLES

The aim of the following examples is to illustrate the various subjects of the present invention and, consequently, they are in no way limiting in nature.

The constructs described below are prepared according to general techniques of genetic engineering and molecular cloning, detailed in Maniatis et al. (1989, Laboratory Manual, Cold Spring Harbor, Laboratory Press, Cold Spring Harbor, N.Y.) or according to the manufacturer's recommendations when a commercial kit is used. The cloning steps using bacterial plasmids are preferably carried out in the *E. coli* strain 5K (Hubacek and Glover, 1970, J. Mol. Biol. 50, 111-127) or BJ 5183 (Hanahan, 1983, J. Mol. Biol. 166, 557-580). The latter strain is preferentially used for the homologous recombination steps. The NM522 strain (Stratagene) is suitable for propagating the M13 phage vectors. The PCR amplification techniques are known to those skilled in the art (see, for example, PCR Protocols—A guide to methods and applications, 1990, edited by Innis, Gelfand, Sninsky and White, Academic Press Inc.). As regards the repair of restriction sites, the technique used consists in filling in the protruding 5' ends using the *E. coli* DNA polymerase I large fragment (Klenow). The Ad5 nucleotide sequences are those used in the Genbank databank under the reference M73260.

As regards the cell biology, the cells are transfected according to the standard techniques known to those skilled in the art. Mention may be made of the calcium phosphate technique (Maniatis et al., above), but any other protocol may also be used, such as the DEAE-dextran technique, electroporation, methods based on osmotic shocks, microinjection or methods based on the use of cationic lipids. As regards the culturing conditions, they are conventional. In the examples which follow, use is made of the 293 human line (ATCC CRL1573) and of the Swiss 3T3 (ATCC CCL92), NR6 (Wells et al., 1990, Science 247: 962-964) and NR6-hEGFR (Schneider et al., 1986, Proc. Natl. Acad. Sci. USA 83, 333-336) murine lines. It is understood that other cell lines may also be used.

Example 1

Construction of an Adenovirus Exhibiting a Host Tropism for Cells Expressing the Receptor for GRP (Gastrin Releasing Peptide)

A. Insertion of the Sequences Encoding the GRP Ligand (Fiber-GRP)

The plasmid pTG6593 derives from p poly II (Lathe et al., 1987, Gene 57, 193-201) by the introduction of the complete gene encoding the Ad5 fiber in the form of an EcoRI-SmaI fragment (nucleotides (nt) 30049 to 33093). The HindIII-SmaI fragment (nt 31994-33093) is isolated and cloned into M13TG130 (Kieny et al., 1983, Gene 26, 91-99) digested with the same enzymes, to give M13TG6526. The latter is subjected to site-directed mutagenesis using the oligonucleotide oTG7000 (SEQ ID NO: 2) (Sculptor in vitro mutagenesis kit, Amersham) in order to introduce a linker encoding a 12 amino acid spacer arm of sequence PSASASASAPGS. The mutated vector thus obtained, M13TG6527, is subjected to a second mutagenesis making it possible to introduce the sequence encoding the 10 residues of the GRP peptide (GNHWAVGHLM; Michael et al., 1995, Gene Ther. 2, 660-668). The oligonucleotide oTG7001 (SEQ ID NO: 3) is used for this purpose. The HindIII-SmaI fragment is isolated from the mutated phage M13TG6528 and introduced, using the homologous recombination technique (Chartier et al., 1996, J. Virol. 70, 4805-4810) into the plasmid pTG6590 carrying the Ad5 adenoviral genome fragment extending from nt 27081 to 35935, and linearized with MunI (nt 32825). The SpeI-ScaI fragment (carrying nt 27082 to 35935 of the Ad5 genome, modified by introducing the spacer arm and the GRP peptide) is isolated from the preceding vector, designated pTG8599, and is then exchanged against the equivalent fragment of pTG6591, digested beforehand with the same enzymes. By way of indication, pTG6591 comprises the wild-type adenoviral sequences from positions 21562 to 35935. pTG4600 is obtained, from which the BstEII fragment (nt 24843 to 35233) is isolated. After homologous recombination with the plasmid pTG3602 which comprises the Ad5 genome (described in greater detail in international application WO 96/17070), the vector pTG4601 is generated.

A cassette which allows expression of the LacZ gene is introduced in place of the E1 adenoviral region by homologous recombination between the plasmid pTG4601 linearized with ClaI and a BsrGI-PstI fragment comprising the LacZ gene encoding β-galactosidase under the control of the Ad2 MLP promoter and the SV40 virus polyadenylation signal. This fragment is isolated from the vector pTG8526 containing the 5' end of the viral genomic DNA (nt 1 to 6241) in which the E1 region (nt 459 to 3328) is replaced with the LacZ expression cassette. The construction thereof is within the scope of those skilled in the art. The final vector is designated pTG4628.

The corresponding viruses AdTG4601 and AdTG4628 are obtained by transfecting the adenoviral fragments released from the plasmid sequences by PacI digestion into the 293 line. By way of indication, AdTG4601 carries the complete Ad5 genome in which the fiber gene comprises, at its 3' end, a spacer arm followed by the GRP peptide. The recombinant virus AdTG4628 also carries the expression cassette for the LacZ reporter gene under the control of the MLP adenoviral promoter.

B. Study of the Tropism of the Virus Bearing the Fiber-GRP

The presence of the GRP peptide on the adenoviral fiber makes it possible to target cells which express the receptor for GRP at their surface. The expression of the messengers encoding this receptor is studied in 293-cells and in Swiss-3T3 murine cells (Zachary et al., 1985, Proc. Natl. Acad. Sci. USA 82, 7616-7620) by Northern blotting. A mixture of 2 DNA fragments complementary to the sequence encoding the receptor for GRP, labeled with the isotope $^{32}P$ using conventional techniques, is used as a probe. By way of indication, the fragments are produced by reverse PCR from total cellular RNA using the oligonucleotides oTG10776 (SEQ ID NO: 4) and oTG10781 (SEQ ID NO: 5) (Battey et al., 1991, Proc. Natl. Acad. Sci. USA 88, 395-399; Corjay et al., 1991, J. Biol. Chem. 266, 18771-18779). The intensity of the mRNAs detected is much greater in the case of the Swiss-3T3 cells than in the 293-cells, indicating overexpression of the GRP receptor by the murine line.

Competition experiments are carried out on the 2 types of cells. The competitor consists of the knob of the Ad5 fiber produced in E. coli, the adenoviral cellular receptor-binding properties of which have been shown (Henry et al., 1994, J. Virol 68, 5239-5246). The cells in monolayer are preincubated for 30 min in the presence of PBS or of increasing concentrations of recombinant Ad5 knob (0.1 to 100 µg/ml) in DMEM medium (Gibco BRL) supplemented with 2% fetal calf serum (FCS). The AdTG4628 virus, the fiber of which contains the GRP peptide, is then added at a multiplicity of infection of 0.001 infectious unit/cell for 24 h at 37° C. The recombinant AdLacZ virus (Stratford-Perricaudet et al., 1992, J. Clin. Invest. 90, 626-630), which carries a gene for the native fiber, is used as a control and under the same experimental conditions. The cells are then fixed and the expression of the LacZ gene is evaluated (Sanes et al., 1986, EMBO J. 5, 3133-3142). The number of blue cells is representative of the efficiency of the viral infection. Inhibition by competition results in a decrease in the number of colored cells compared to a noninfected control (PBS).

The addition of recombinant Ad5 knob at a concentration of 100 µg/ml strongly inhibits the infection of the 293-cells with the AdLacZ and AdTG4628 viruses (degree of inhibition of 95 and 98%). This suggests that the presence of the competitor prevents the interaction of the adenoviral fiber with its natural cellular receptor. On the other hand, the two viruses behave differently on the Swiss-3T3 cells. The infection of the AdTG4628 virus in the presence of 100 µg/ml of competitor is only partially inhibited, whereas, under the same experimental conditions, that of the AdLacZ virus, which has the native fiber, is totally inhibited. These results suggest that the infection of the Swiss-3T3 cells with AdTG4628 is, in part, mediated by an independent receptor, probably the GRP receptor, which these cells overexpress. In conclusion, adding the GRP ligand to the C-terminal end of the fiber promotes infection of cells expressing the GRP receptor, independently of the natural cellular receptor-fiber interaction.

Example 2

Construction of an Adenovirus Exhibiting a Tropism for Tumor Cells Expressing Mucins Construction: insertion of the EPPT peptide, as described in U.S. Pat. No. 5,591,593, at the C-terminal end of the fiber. This modification confers binding with regard to the mucins overexpressed on tumor cells.

For this, the vector M13TG6572 was obtained using the oligonucleotide OTG11992: SEQ ID NO: 38 and by applying the mutagenesis procedure presented in Example 1 using the vector M13TG6527. Homologous recombination was performed with pTG4213 (see Example 4) to give pTG4278.

Example 3

Construction of an Adenovirus Exhibiting a Tropism for Tumor Cells Expressing β4 β1 aintegrins Construction: insertion of the LDV peptide, as described in U.S. Pat. No. 5,628,979, at the C-terminal end of the fiber. This modification confers binding with regard to the α4β1 integrins overexpressed on tumor cells.

For this, the vector M13TG13265 was obtained using the oligonucleotide OTG11991: SEQ ID NO: 39 and by applying the mutagenesis procedure presented in Example 1 using the vector M13TG6527.

Example 4

Construction of an Adenovirus Exhibiting a Host Tropism for Cells Expressing the EGF (Epidermal Growth Factor) Receptor This example describes a fiber bearing the EGF sequences at its C-terminal end. For this, the oligonucleotides oTG11065 (SEQ ID NO: 6) and oTG11066 (SEQ ID NO: 7) are used to amplify a HindIII-XbaI fragment from the plasmid M13TG6527. The oligonucleotides oTG11067 (SEQ ID NO: 8) and oTG11068 (SEQ ID NO: 9) make it possible to generate an XhoI-SmaI fragment (ranging from the stop codon to nt 33093) from M13TG6527. The EGF complementary DNA, obtained from the ATCC (#59957), is amplified in the form of an XhoI-XbaI fragment using the oligonucleotides oTG11069 (SEQ ID NO: 10) and oTG11070 (SEQ ID NO: 11). The 3 fragments digested with the appropriate enzymes are then religated to give a HindIII-SmaI fragment containing the EGF fused to the C-terminal end of the fiber. The same homologous recombination procedure as that described in Example 1 is applied in order to replace this fragment into its genomic context.

However, it is possible to simplify the cloning steps by introducing a unique BstBI site into the targeted region by conventional techniques of mutagenesis on the matrix M13TG6526 using the oligo oTG7213 (SEQ ID NO: 57). At the end of the successive cloning steps as described in Example 1, the plasmid pTG4609, carrying the entire genome of the modified Ad5 is obtained. Its equivalent carrying the LacZ expression cassette in place of the E1 region is obtained as previously described in Example 1 and is named pTG4213. Homologous recombination between pTG4609 or pTG4213, linearized with BstBI, and the previous HindIII-SmaI fragment generates the plasmid pTG4225 and pTG4226 carrying, respectively, the wild-type E1 region or the LacZ expression cassette. The AdTG4225 and AdTG4226 viruses can be produced conventionally by transfecting a suitable cell line, for example overexpressing the receptor for EGF.

To test the specificity of infection of these viruses, use may be made of NR6 murine fibroblast cells and NR6-hEGFR cells expressing the receptor for human EGF. Competitions with the recombinant Ad5 knob or with EGF make it possible to evaluate the involvement of the EGF and natural cellular receptors in mediating the infection of the viruses.

Example 5

Modifications of the Fiber Knob in Order to Eliminate Binding to the Natural Cellular Receptor Mutation of the region of the adenoviral fiber involved in the interaction with the natural cellular receptor was undertaken in order to eliminate the ability of the fiber to bind its natural receptor and addition of a ligand will make it possible to modify the tropism of the corresponding adenoviruses.

The Ad5 fiber sequences encoding the region extending from residues 443 to 462 was subjected to various mutations. Deletion of sheet D uses the mutagenesis oligonucleotide oTG7414 (SEQ ID NO: 12) and deletion of loop CD uses the oligonucleotide OTGA (SEQ ID NO: 13). As regards the oligonucleotide OTGB (SEQ ID NO: 14), it allows deletion of loop CD and sheet D. All these oligonucleotides contain a BamHI site which makes it possible to readily detect the mutants and also to insert the sequences encoding a ligand, for example the EGF peptide.

Another series of modifications consists in replacing these deleted regions with the equivalent sequences derived from the Ad3 fiber. In fact, many data show that Ad5 and Ad3 do not bind to the same receptor, so that such a substitution should abolish infection mediated by the Ad5 receptor and target cells bearing the Ad3 receptor. The replacement of the Ad5 loop CD with that of Ad3 uses oTG11135 (SEQ ID NO: 15), the replacement of sheet D of the Ad5 fiber with that of the Ad3 fiber is produced using the oligonucleotide oTG10350 (SEQ ID NO: 16) and the replacement of sheet D and of loop CD of Ad5 with those of Ad3 is carried out on the previous mutant using oTG11136 (SEQ ID NO: 17).

This target region of the adenoviral knob is also modified via a series of point mutations:

replacement of bend aa GSLA with bend aa DKLT: oTGC (SEQ ID NO: 18),
replacement of bend aa SGTV with bend aa DKLT: OTGD (SEQ ID NO: 19),
G443 to D: OTGE (SEQ ID NO: 20),
L445 to F: OTGF (SEQ ID NO: 21),
G450 to N: OTGG (SEQ ID NO: 22),
T451 to K: OTGH (SEQ ID NO: 23),
V452 to N: OTGI (SEQ ID NO: 24),
A455 to F: OTGJ (SEQ ID NO: 25),
L457 to A: OTGK (SEQ ID NO: 26),
1459 to A: OTGL (SEQ ID NO: 27).

oTGE to I introduce mutations in loop CD of the adenoviral fiber on amino acids which are nonconservative between Ad5 and Ad3, while OTGJ to K concern amino acids of sheet D which are not involved in a hydrogen bond which stabilizes the structure.

The mutageneses may be carried out on the vector M13TG6526 or M13TG6528. The first carries the wild-type HindIII-SmaI fragment and the second carries this same fragment modified by insertion of the GRP sequences. The plasmids carrying the adenoviral genome may be reconstituted as described previously for the plasmids pTG4225 (wild-type E1) and pTG4226 (LacZ in place of the E1 region). The viruses are generated by transfecting 293-cells or cells overexpressing the receptor which binds the ligand concerned. Such cells may be generated by transfecting the corresponding complementary DNA. Cells which do not naturally express the natural cellular receptor for adenoviruses are preferably used, for example the Daudi line (ATCC CCL213).

Example 6

Modification of the Fiber Knob in Order to Eliminate Binding to the Natural Cellular Receptor A. Modifications of the Fiber Sequences Mutation of the AB region (residues 404-418) of the adenoviral fiber was undertaken in order to eliminate the ability of the fiber to bind its natural receptor and addition of a ligand will make it possible to modify the tropism of the corresponding adenoviruses.

replacement, in loop AB, of the serine at position 408 with the glutamic acid residue of serotype 3 using the oligo oTG12499 (SEQ ID NO: 40);
replacement, in loop AB, of the alanine at position 406 with the lysine residue of serotype 3 using the oligo oTG12498 (SEQ ID NO: 41);
replacement, in loop AB, of the threonine at position 404 with the glycine residue of serotype 3 using the oligo oTG12740 (SEQ ID NO: 42).

The mutageneses may be carried out on the vector M13TG6526 or M13TG6528. The first carries the wild-type HindIII-SmaI fragment and the second carries this same fragment modified by insertion of the GRP sequences. The plasmids carrying the adenoviral genome may be reconstituted as described beforehand for the plasmids pTG4225 (wild-type E1) and pTG4226 (LacZ in place of the E1 region) (homologous recombination with the plasmid pTG4609 or pTG4213). The viruses are generated by transfecting 293-cells, 293-cells expressing the wild-type fiber (Legrand et al., 1999; J. Virol., 73, 907-919) or cells overexpressing the receptor which binds the ligand concerned. Such cells may be generated by transfecting the corresponding complementary DNA. Cells which do not naturally express the natural cellular receptor for adenoviruses are preferably used, for example the Daudi line (ATCC CCL213).

| Mutation | Oligo oTG- | M13 M13TG | Plasmid pTG- |
|---|---|---|---|
| Loop AB (404-418); 404TPAPS408 | | | |
| 404GPAPS408 | 12740 (SEQ ID NO:42) | 14017 | 14283 |
| 404TPKPS408 | 12498 (SEQ ID NO:41) | 6587 | 4289 |
| 404TPAPE408 | 12499 (SEQ ID NO:40) | 6588 | 4291 |

B. Study of the Incorporation of the Modified Fiber into the Viral Particle and of its Use in the Entry of the Corresponding Adenovirus In order to be sure that the mutated viruses indeed bear the modified fiber proteins within their capsid, the viruses purified after amplification in 293-cells are loaded onto a 10% acrylamide gel under denaturing conditions (SDS-PAGE). The various proteins are detected by silver nitrate staining. Alternatively, the fiber is specifically revealed by performing Western blotting using a serum directed against the knob of the Ad5 fiber (Henry et al., 1994, above). An intense signal at the expected size indicates that the viruses incorporate stoichiometric amounts of the protein of interest. Given that only the trimeric fiber is capable of binding the penton base (Novelli and Boulanger, 1991, above) and of being incorporated into the particle, detection of the protein in the experiment above indicates that the modified fiber is still capable of forming trimers.

The use of the modified fiber to allow entry of the corresponding mutated virus may be studied by carrying out competition experiments using recombinant knob as described in example 1B. An efficient infection in the presence of saturating concentrations of the wild-type peptide indicates an infection independent of binding to the natural primary receptors. This suggests a greatly decreased affinity of the modified fiber for its receptors.

Example 7

Insertion of the Ligand into a Capsid Protein Other Than the Fiber in Combination with One of the Abovementioned Modifications of the Fiber This example describes the insertion of the EGF ligand into the hexon capsid protein. Of course, it is preferable for the corresponding adenovirus to have lost its ability to attach to the natural cellular receptor. Its genome may, for example, include a modified fiber gene or lack at least part of the fiber sequences.

A transfer plasmid for the homologous recombination is constructed which covers the region of the Ad5 genome encoding the hexon (nt 18842-21700). The HindIII-XhoI fragment (nt 18836-24816) of Ad5 is cloned into pBSK+ (Stratagene) digested with the same enzymes, to give the plasmid pTG4224. The sequences encoding the EGF peptide are introduced into the hypervariable loop L1 of the hexon by creating chimeric fragments by PCR: hexon (nt19043-19647)-XbaI-EGF-BsrGI-hexon (nt196990-20312). The fragment nt19043 to 19647 is obtained by PCR amplification using the plasmid pTG3602 with the oligonucleotides oTG11102 (SEQ ID NO: 28) and oTG11103 (SEQ ID NO: 29). The fragment nt19699 to 20312 is amplified from the same DNA with the oligonucleotides oTG11104 (SEQ ID NO: 30) and oTG11105 (SEQ ID NO: 31). The EGF is cloned using the cDNA with the oligonucleotides oTG11106 (SEQ ID NO: 32) and oTG11107 (SEQ ID NO: 33) making it possible to place the EGF coding sequence in frame with the hexon. The PCR products are digested with the appropriate enzymes and then religated. The chimeric fragment can then be inserted, by homologous recombination, into the plasmid pTG4224 linearized with NdeI (nt 19549), to give pRG4229. The sequences encoding the modified hexon can then be obtained by HindIII/XhoI digestion and re-placed into the genomic context by homologous recombination. It is possible to use the vector pTG3602, pTG4607 or pTG4629, linearized with SgfI, or a vector carrying the adenoviral genome deleted of the fiber sequences (such as pTG4607 described below) or expressing a modified fiber.

The adenoviral genome incapable of producing a functional native fiber is obtained through a deletion which affects the initiating codon but does not extend to the other adenoviral ORFs. The following procedure is carried out: the adenoviral fragment in 5' of the deletion (nt 30564 to 31041) is amplified by PCR using the primers oTG7171 and oTG7275 (SEQ ID NOs: 34 and 35). The amplification of the fragment in 3' (nt 31129 to 33099) uses the primers oTG7276 and oTG7049 (SEQ ID NOs: 36 and 37). The PCR fragments are digested with XhoI and ligated, before being introduced, by homologous recombination, into the vector pTG6591 linearized with NdeI, to give pTG4602. The BstEII fragment is then isolated from this plasmid and subjected to homologous recombination with the vector pTG3602 digested with SpeI.

pTG4607 is obtained. The vector pTG4629 is equivalent to pTG4607, but also carries the LacZ expression cassette in place of E1.

The corresponding viruses may be obtained after transfection of 293-cells, 293-cells expressing the wild-type fiber (Legrand et al., 1999, above) or cells overexpressing the receptor for EGF. The study of the specificity of infection may be carried out as described previously using EGF as the competitor (see example 1).

Example 8

Construction of an Adenovirus Exhibiting a Tropism for Cells Expressing Particular Glycoproteins, Namely Heparan Sulfate Glycoproteins This example describes a fiber bearing seven lysine residues located after the linker polypeptide (PSASASASAPGS) encoded by SEQ ID NO: 2, at the C-terminal end, and which confer the property of attaching to glycoproteins termed "heparan sulfate glycoproteins". To this effect, the oligonucleotide oTG12125 (SEQ ID NO: 43) is hybridized to the construct M13TG6527 in order to generate, by mutagenesis, the construct M13TG6570. The step of homologous recombination between the plasmid pTG4213 linearized by cleavage with BstBI and the HindIII-SmaI fragment of M13TG6570 makes it possible to obtain the plasmid pTG4274. The corresponding adenoviral virus AdTG4274 is obtained after transfecting said plasmid into the 293 complementation line and culturing under the usual culture conditions. In order to evaluate the specificity of infection with this virus, competition experiments with a recombinant adenovirus may be carried out (example 1).

Example 9

Construction of an Adenovirus Exhibiting a Host Specificity Directed Toward Tumor Cells Expressing Mucins This example describes the production of a fiber, bearing at its C-terminal end, the EPPT peptide (described in U.S. Pat. No. 5,591,593) which confers specificity for the mucins overexpressed at the surface of certain tumor cells. The construct M13TG6527 is subjected to a step of site-directed mutagenesis using the oligonucleotide [lacuna] (SEQ ID NO: 44) in order to generate the construct M13TG6572. The plasmid pTG4278 is obtained according to the procedure described above. The mutation is introduced into the viral genome as described in example 8. The virus AdTG4278 is produced after transformation and culturing in the 293 line. Competition experiments for the viral infection using the adenoviral knob and with the soluble EPPT peptide show that it is possible to evaluate the involvement of the natural cellular receptors and of mucins in the infectious process of the adenovirus.

Example 10

Construction of an Adenovirus Exhibiting a Specificity for Tumor Cells Expressing the α4β1 Integrins This example describes an adenoviral fiber bearing the LDV peptide sequence (see U.S. Pat. No. 5,628,979) at its C-terminal end in order to confer, on the protein, the ability to attach to the expressing the α4β1 integrins which are overexpressed at the surface of certain tumor cells. For this, the vector M13TG6527 is subjected to a step of site-directed mutagenesis using oTG11991 (SEQ ID NO: 45) in order to generate the modified vector M13TG13265. This mutation is incorporated into the viral genome according to the protocol described in example 6. The virus is then produced using the 293 complementation line. Competition experiments are carried out according to the protocol described in example 1 using the knob of the Ad5 fiber produced in *E. coli*, the adenoviral cellular receptor-binding properties of which have been shown (Henry et al., 1994, J. Virol 68, 5239-5246) or using soluble peptides comprising the LDV sequence which make it possible to evaluate the infectious capacity of the adenoviruses mediated by attachment to the α4β1 integrins.

Example 11

Modification of the Fiber Knob so as to Eliminate Attachment to its Natural Cellular Receptor The mutations described above were more particularly intended to prevent attachment to MHC-I molecules. In order to substantially decrease the attachment to CAR, other mutations were produced. Three-dimensional analysis of the structure of the knob and comparison of the sequences of adenoviral fibers derived from CAR-serotypes and non-CAR-serotypes (Roelvink et al., 1998, J. Virol. 72, 7909-7915) have led us to identify more specifically the amino acids involved in the recognition of an attachment to CAR. These residues were modified as shown below (indicated between brackets are the oligonucleotides used in the site-directed mutagenesis experiments):

Tyr 491 to Asp (Y491D): oTG12727 (SEQ ID NO: 46)
Ala 494 to Asp (A494D): oTG12728 (SEQ ID NO: 47)
Val 495 to Arg (V495R): oTG12729 (SEQ ID NO: 48)
Gly 496 to Ser (G496S): oTG12730 (SEQ ID NO: 49)
Phe 497 to Asp (F497D): oTG12731 (SEQ ID NO: 50)
Met 498 to Asp (M498D): oTG12732 (SEQ ID NO: 51)
Pro 499 to Gly (P499G): oTG12733 (SEQ ID NO: 52)
Asn 500 to Asp (N500D): oTG12734 (SEQ ID NO: 53)
Ala 503 to Asp (A503D): oTG12735 (SEQ ID NO: 54)
Tyr 504 to Asp (Y504D): oTG12736 (SEQ ID NO: 55)
Pro 505 to Gly (P505G): oTG12737 (SEQ ID NO: 56).

The mutageneses are carried out using the vectors M13TG6526, M13TG6528, M13TG6570, M13TG6572 or M13TG13265 described in the previous examples. The plasmids carrying the adenoviral genome are produced as indicated previously and the viral particles are obtained by transfection and culturing in:

the 293 cell line,
or the 293 cell line expressing the wild-type adenoviral fiber (Legrand et al., 1999, J. Virol. 73, 907-919),
or cells overexpressing the receptor corresponding to the ligand used. Such cells may be generated by transfection with the corresponding cDNA. However, use is preferably made of cells which do not express the natural adenoviral receptor, such as, for example, the Daudi line (ATCC CCL213) or CHO line (ATCC CcI61).

In order to verify that the mutated viruses indeed bear, within their capsid, the protein of the modified fiber according to the invention, the modified viral particles are loaded onto a 10% SDS polyacrylamide gel. The various viral proteins are revealed by silver staining. The fiber protein is then specifically tested by western blotting using antibodies directed against the adenoviral knob (Henry et al., 1994, above). In the present case, a strong signal is observed for a band the migration of which corresponds to the expected size. This clearly shows that the viruses have incorporated a stoichiometric amount of mutated fiber while being produced. Given that only the fiber in its trimeric form can bind the penton base and then be encapsidated (Novelli and Boulanger, 1991, above), the presence of this signal at the expected position indicates that the modified fiber according to the invention is still capable of trimerization.

The invention claimed is:

1. A substantially purified adenovirus fiber comprising SEQ ID NO: 1, except that at least one of the alanine residue at position 494 of SEQ ID NO: 1 and the alanine residue at position 503 of SEQ: ID NO: 1 is modified by substitution;
   wherein the binding of the adenovirus fiber to the natural cellular receptor for adenovirus serotype Ad5 is inhibited or prevented.

2. The adenovirus fiber of claim 1, wherein
   (a) the alanine residue at position 494 of SEQ ID NO: 1 is substituted with an aspartic acid, and
   (b) the alanine residue at position 503 of SEQ ID NO: 1 is substituted with an aspartic acid.

3. A substantially purified adenovirus fiber comprising SEQ ID NO: 1, except that:
   (a) at least one of the alanine residue at position 494 of SEQ ID NO: 1 and the alanine residue at position 503 of SEQ: ID NO: 1 is modified by substitution; and
   (b) the serine residue at position 408 of SEQ ID NO: 1 is substituted with a residue having at least two carboxyl groups,
   wherein the binding of the adenovirus fiber to the natural cellular receptor for adenovirus serotype Ad5 is inhibited or prevented.

4. The adenovirus fiber of claim 3, wherein the serine residue at position 408 of SEQ ID NO: 1 is substituted with an aspartic acid or a glutamic acid.

5. The adenovirus fiber of claim 4, wherein the serine residue at position 408 of SEQ ID NO: 1 is substituted with an aspartic acid.

6. The adenovirus fiber of claim 4, wherein the serine residue at position 408 of SEQ ID NO: 1 is substituted with a glutamic acid.

7. The adenovirus fiber of claim 1 or 3, further comprising a targeting element.

8. The adenovirus fiber of claim 7, wherein the targeting element is selected from the group consisting of an antibody, an antibody fragment, a peptide, an oligonucleotide, a lipid, a glycolipid, a hormone, a polymer and a sugar.

9. A substantially purified viral particle which lacks a functional native fiber, and comprises the adenovirus fiber of claim 1 or 3.

10. The viral particle of claim 9, further comprising a targeting element.

11. The viral particle of claim 10, wherein the targeting element is inserted into an adenoviral capsid protein other than the fiber.

12. The viral particle of claim 9, wherein the viral particle is an empty pseudoparticle.

13. The viral particle of claim 9, which comprises an adenoviral genome.

14. The viral particle of claim 13, wherein said adenoviral genome is a replication-defective recombinant adenoviral genome.

15. A method for producing the viral particle as claimed in claim 14, wherein:
   (i) said replication-defective recombinant adenoviral genome is transfected into a suitable cell line,
   (ii) said transfected cell line is cultured under suitable conditions so as to allow the production of said adenoviral particle,
   (iii) said viral particle is recovered from said transfected cell line and, optionally,
   (iv) said adenoviral particle is purified.

16. A composition comprising the viral particle of claim 9, in combination with a pharmaceutically acceptable support.

17. The composition of claim 16, further comprising at least one compound comprising a naked nucleic acid or a nucleic acid combined with at least one cationic compound.

* * * * *